United States Patent
Saadat et al.

(10) Patent No.: US 11,026,738 B2
(45) Date of Patent: Jun. 8, 2021

(54) DEVICES AND METHODS FOR TREATING A LATERAL SURFACE OF A NASAL CAVITY

(71) Applicant: Arrinex, Inc., Redwood City, CA (US)

(72) Inventors: Vahid Saadat, Atherton, CA (US); William Jason Fox, San Mateo, CA (US); Mojgan Saadat, Atherton, CA (US)

(73) Assignee: Arrinex, Inc., Redwood City, CA (US)

( * ) Notice: Subject to any disclaimer, the term of this patent is extended or adjusted under 35 U.S.C. 154(b) by 292 days.

(21) Appl. No.: 15/624,632

(22) Filed: Jun. 15, 2017

(65) Prior Publication Data
US 2018/0125560 A1    May 10, 2018

Related U.S. Application Data

(60) Provisional application No. 62/350,445, filed on Jun. 15, 2016.

(51) Int. Cl.
*A61B 18/02* (2006.01)
*A61B 17/24* (2006.01)
(Continued)

(52) U.S. Cl.
CPC .............. *A61B 18/02* (2013.01); *A61B 17/24* (2013.01); *A61B 2017/003* (2013.01);
(Continued)

(58) Field of Classification Search
CPC ... A61B 18/02; A61B 17/24; A61B 2017/003; A61B 2017/00867; A61B 2017/00946;
(Continued)

(56) References Cited

U.S. PATENT DOCUMENTS

| 604,554 A | 5/1898 | Wise et al. |
|---|---|---|
| 2,662,046 A | 12/1953 | Howe et al. |

(Continued)

FOREIGN PATENT DOCUMENTS

| EP | 2532300 | 12/2012 |
|---|---|---|
| EP | 2662027 | 11/2013 |

(Continued)

OTHER PUBLICATIONS

Bicknell et al., "Cryosurrgery for Allergic and Vasomotor Rhinitis", The Journal of Laryngology and Otology, vol. 93, Feb. 1979, 143-146.

(Continued)

*Primary Examiner* — Michael F Peffley
*Assistant Examiner* — Tigist S Demie
(74) *Attorney, Agent, or Firm* — McDonnell Boehnen Hulbert & Berghoff LLP

(57) ABSTRACT

The invention disclosed here generally relates to devices that can modify a property of a nerve. Specifically, the subject invention is contemplated to modify the posterior nasal nerve signal conduction in such a way so as to reduce the signals transmitted to the nasal cavity. Reduction or interruption of the nerve signals results in the reduction of the distal organ activity. In particular, embodiments of the present invention allow for increased lateral contact or apposition of the target tissue region having at least one posterior nasal nerve with the end effector surface by lateral and/or longitudinal translation of the end effector relative to the surgical probe shaft. This improved lateral surface contact has several benefits, including improved patient outcomes and patient safety as the end effector is adequately in contact with target tissue for subsequent ablation therapy.

43 Claims, 21 Drawing Sheets

(51) Int. Cl.
*A61B 17/00* (2006.01)
*A61B 18/00* (2006.01)

(52) U.S. Cl.
CPC .............. *A61B 2017/00867* (2013.01); *A61B 2017/00946* (2013.01); *A61B 2017/00991* (2013.01); *A61B 2018/0022* (2013.01); *A61B 2018/00196* (2013.01); *A61B 2018/00327* (2013.01); *A61B 2018/00434* (2013.01); *A61B 2018/00577* (2013.01); *A61B 2018/0212* (2013.01); *A61B 2018/0231* (2013.01)

(58) Field of Classification Search
CPC .. A61B 2017/0091; A61B 2018/00196; A61B 2018/0022; A61B 2018/00327; A61B 2018/00434; A61B 2018/00577; A61B 2018/0212; A61B 2018/0231
See application file for complete search history.

(56) References Cited

U.S. PATENT DOCUMENTS

| | | | |
|---|---|---|---|
| 2,662,116 A | | 12/1953 | Xavier-Noel et al. |
| 5,472,441 A | | 12/1995 | Edwards et al. |
| 5,486,161 A | | 1/1996 | Sharkey et al. |
| 5,527,351 A | | 6/1996 | Friedman et al. |
| 5,611,796 A | | 3/1997 | Kamami |
| 5,669,903 A | * | 9/1997 | O'Donnell ............. A61B 18/02 128/898 |
| 5,718,702 A | | 2/1998 | Edwards et al. |
| 5,733,280 A | | 3/1998 | Avitall |
| 5,899,898 A | | 5/1999 | Arless et al. |
| 5,899,899 A | | 5/1999 | Arless et al. |
| 5,935,123 A | | 8/1999 | Edwards et al. |
| 5,971,979 A | | 10/1999 | Joye et al. |
| 6,053,172 A | * | 4/2000 | Hovda ............... A61B 18/1402 128/898 |
| 6,106,518 A | | 8/2000 | Wittenberger et al. |
| 6,210,355 B1 | | 4/2001 | Edwards et al. |
| 6,270,476 B1 | | 8/2001 | Santoianni et al. |
| 6,277,064 B1 | | 8/2001 | Yoon et al. |
| 6,283,959 B1 | | 9/2001 | Lalonde et al. |
| 6,355,029 B1 | | 3/2002 | Joye et al. |
| 6,375,654 B1 | | 4/2002 | McIntyre |
| 6,428,534 B1 | | 8/2002 | Joye et al. |
| 6,432,102 B2 | | 8/2002 | Joye et al. |
| 6,514,245 B1 | | 2/2003 | Williams et al. |
| 6,517,533 B1 | | 2/2003 | Swaminathan |
| 6,537,271 B1 | | 3/2003 | Murray et al. |
| 6,575,966 B2 | | 6/2003 | Lane et al. |
| 6,595,988 B2 | | 7/2003 | Wittenberger et al. |
| 6,602,276 B2 | | 8/2003 | Dobak, III et al. |
| 6,648,879 B2 | | 11/2003 | Joye et al. |
| 6,666,858 B2 | | 12/2003 | Lafontaine |
| 6,673,066 B2 | | 1/2004 | Werneth |
| 6,685,732 B2 | | 2/2004 | Kramer |
| 6,736,809 B2 | | 5/2004 | Capuano et al. |
| 6,786,900 B2 | | 9/2004 | Joye et al. |
| 6,786,901 B2 | | 9/2004 | Joye et al. |
| 6,811,550 B2 | | 11/2004 | Holland et al. |
| 6,837,888 B2 | | 1/2005 | Ciarrocca et al. |
| 6,875,209 B2 | | 4/2005 | Zvuloni et al. |
| 6,905,494 B2 | | 6/2005 | Yon et al. |
| 6,908,462 B2 | | 6/2005 | Joye et al. |
| 6,949,096 B2 | | 9/2005 | Davison et al. |
| 6,972,015 B2 | | 12/2005 | Joye et al. |
| 6,989,009 B2 | | 1/2006 | Lafontaine |
| 6,991,631 B2 | | 1/2006 | Woloszko et al. |
| 7,001,378 B2 | | 2/2006 | Yon et al. |
| 7,060,062 B2 | | 6/2006 | Joye et al. |
| 7,081,112 B2 | | 7/2006 | Joye et al. |
| 7,101,368 B2 | | 9/2006 | Lafontaine |
| 7,104,984 B2 | | 9/2006 | Ryba et al. |
| 7,189,227 B2 | | 3/2007 | Lafontaine |
| 7,288,089 B2 | | 10/2007 | Yon et al. |
| 7,291,144 B2 | | 11/2007 | Dobak, III et al. |
| 7,300,433 B2 | | 11/2007 | Lane et al. |
| 7,354,434 B2 | | 4/2008 | Zvuloni et al. |
| 7,418,292 B2 | | 8/2008 | Shafer et al. |
| 7,442,190 B2 | | 10/2008 | Abboound et al. |
| 7,449,018 B2 | | 11/2008 | Kramer |
| 7,527,622 B2 | | 5/2009 | Lane et al. |
| 7,641,679 B2 | | 1/2010 | Joye et al. |
| 7,648,497 B2 | | 1/2010 | Lane et al. |
| 7,727,191 B2 | | 6/2010 | Mihalik et al. |
| 7,727,228 B2 | | 6/2010 | Abboud et al. |
| 7,740,627 B2 | | 6/2010 | Gammie et al. |
| 7,769,442 B2 | | 8/2010 | Shafer et al. |
| 7,794,455 B2 | | 9/2010 | Abboud et al. |
| 7,842,031 B2 | | 11/2010 | Abboud et al. |
| 7,862,557 B2 | | 1/2011 | Joye et al. |
| 7,892,230 B2 | | 2/2011 | Woloszko |
| 8,043,283 B2 | | 10/2011 | Dobak, III et al. |
| 8,043,351 B2 | | 10/2011 | Yon et al. |
| 8,088,127 B2 | | 1/2012 | Mayse et al. |
| 8,142,424 B2 | | 3/2012 | Swanson et al. |
| 8,157,794 B2 | | 4/2012 | Dobak, III et al. |
| 8,177,779 B2 | | 5/2012 | Joye et al. |
| 8,187,261 B2 | | 5/2012 | Watson |
| 8,231,613 B2 | | 7/2012 | Baxter et al. |
| 8,235,976 B2 | | 8/2012 | Lafontaine |
| 8,292,887 B2 | | 10/2012 | Woloszko et al. |
| 8,298,217 B2 | | 10/2012 | Lane et al. |
| 8,333,758 B2 | | 12/2012 | Joye et al. |
| 8,382,746 B2 | | 2/2013 | Williams et al. |
| 8,382,747 B2 | | 2/2013 | Abboud et al. |
| 8,388,600 B1 | | 3/2013 | Eldredge et al. |
| 8,394,075 B2 | | 3/2013 | Ansarinia et al. |
| 8,425,456 B2 | | 4/2013 | Mihalik et al. |
| 8,425,457 B2 | | 4/2013 | John et al. |
| 8,439,906 B2 | | 5/2013 | Watson |
| 8,465,481 B2 | | 6/2013 | Mazzone et al. |
| 8,475,440 B2 | | 7/2013 | Abboud et al. |
| 8,480,664 B2 | | 7/2013 | Watson et al. |
| 8,491,636 B2 | | 7/2013 | Abboud et al. |
| 8,512,229 B2 | | 8/2013 | Saadat et al. |
| 8,512,324 B2 | | 8/2013 | Abboud et al. |
| 8,545,491 B2 | | 10/2013 | Abboud et al. |
| 8,591,504 B2 | | 11/2013 | Tin |
| 8,617,149 B2 | | 12/2013 | Lafontaine et al. |
| 8,632,529 B2 | | 1/2014 | Bencini |
| 8,663,211 B2 | | 3/2014 | Fourkas et al. |
| 8,672,930 B2 | | 3/2014 | Wittenberger |
| 8,676,324 B2 | | 3/2014 | Simon et al. |
| 8,679,104 B2 | | 3/2014 | Abboud et al. |
| 8,679,105 B2 | | 3/2014 | Wittenberger et al. |
| 8,715,274 B2 | | 5/2014 | Watson |
| 8,715,275 B2 | | 5/2014 | Burger et al. |
| 8,747,401 B2 | | 6/2014 | Gonzalez et al. |
| 8,764,740 B2 | | 7/2014 | Watson |
| 8,771,264 B2 | | 7/2014 | Abboud et al. |
| 8,827,952 B2 | | 9/2014 | Subramaniam et al. |
| 8,900,222 B2 | | 12/2014 | Abboud et al. |
| 8,911,434 B2 | | 12/2014 | Wittenberger |
| 8,926,602 B2 | | 1/2015 | Pageard |
| 8,936,594 B2 | | 1/2015 | Wolf et al. |
| 8,945,107 B2 | | 2/2015 | Buckley et al. |
| 8,986,293 B2 | | 3/2015 | Desrochers |
| 8,986,301 B2 | | 3/2015 | Wolf et al. |
| 8,996,137 B2 | | 3/2015 | Wardle et al. |
| 9,050,073 B2 | | 6/2015 | Newell et al. |
| 9,050,074 B2 | | 6/2015 | Joye et al. |
| 9,060,754 B2 | | 6/2015 | Buckley et al. |
| 9,060,755 B2 | | 6/2015 | Buckley et al. |
| 9,066,713 B2 | | 6/2015 | Turovskiy |
| 9,072,597 B2 | | 7/2015 | Wolf et al. |
| 9,084,590 B2 | | 7/2015 | Wittenberger et al. |
| 9,084,592 B2 | | 7/2015 | Wu et al. |
| 9,089,314 B2 | | 7/2015 | Wittenberger |
| 9,168,079 B2 | | 10/2015 | Lalonde |
| 9,168,081 B2 | | 10/2015 | Williams et al. |
| 9,179,964 B2 | | 11/2015 | Wolf et al. |
| 9,179,967 B2 | | 11/2015 | Wolf et al. |
| 9,211,393 B2 | | 12/2015 | Hu et al. |

(56) References Cited

U.S. PATENT DOCUMENTS

| | | |
|---|---|---|
| 9,220,556 B2 | 12/2015 | Lalonde et al. |
| 9,237,924 B2 | 1/2016 | Wolf et al. |
| 9,241,752 B2 | 1/2016 | Nash et al. |
| 9,254,166 B2 | 2/2016 | Aluru et al. |
| 9,265,956 B2 | 2/2016 | Ackermann et al. |
| 9,333,023 B2 | 5/2016 | Wittenberger |
| 9,414,878 B1 | 8/2016 | Wu et al. |
| 9,415,194 B2 | 8/2016 | Wolf et al. |
| 9,433,463 B2 | 9/2016 | Wolf et al. |
| 9,439,709 B2 | 9/2016 | Duong et al. |
| 9,439,727 B2 | 9/2016 | Govari et al. |
| 9,445,859 B2 | 9/2016 | Pageard |
| 9,452,010 B2 | 9/2016 | Wolf et al. |
| 9,480,521 B2 | 11/2016 | Kim et al. |
| 9,486,278 B2 | 11/2016 | Wolf et al. |
| 9,522,030 B2 | 12/2016 | Harmouche et al. |
| 9,526,571 B2 | 12/2016 | Wolf et al. |
| 9,555,223 B2 | 1/2017 | Abboud et al. |
| 9,572,536 B2 | 2/2017 | Abboud et al. |
| 9,801,752 B2 | 10/2017 | Wolf et al. |
| 2002/0049367 A1 | 4/2002 | Irion et al. |
| 2003/0144659 A1 | 7/2003 | Edwards et al. |
| 2004/0024412 A1 | 2/2004 | Clements et al. |
| 2006/0235474 A1 | 10/2006 | Demarais et al. |
| 2006/0276852 A1 | 12/2006 | Demarais et al. |
| 2007/0093710 A1 | 4/2007 | Maschke et al. |
| 2007/0173899 A1 | 7/2007 | Levin et al. |
| 2007/0179380 A1 | 8/2007 | Grossman et al. |
| 2007/0265687 A1 | 11/2007 | Deem et al. |
| 2007/0293726 A1 | 12/2007 | Goldfarb et al. |
| 2007/0299433 A1 | 12/2007 | Williams et al. |
| 2008/0009851 A1 | 1/2008 | Wittenberger et al. |
| 2008/0009925 A1 | 1/2008 | Abboud et al. |
| 2008/0027423 A1 | 1/2008 | Choi et al. |
| 2008/0119693 A1 | 5/2008 | Makower et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0182193 A1 | 7/2009 | Whitman et al. |
| 2009/0182318 A1 | 7/2009 | Abboud et al. |
| 2009/0234345 A1 | 9/2009 | Hon et al. |
| 2010/0030113 A1* | 2/2010 | Morriss .................. A61B 1/233 600/585 |
| 2010/0057150 A1 | 3/2010 | Demarais et al. |
| 2010/0121270 A1 | 5/2010 | Gunday et al. |
| 2010/0137860 A1 | 6/2010 | Demarais et al. |
| 2010/0137952 A1 | 6/2010 | Demarais et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2011/0152855 A1 | 6/2011 | Mayse et al. |
| 2011/0184402 A1 | 7/2011 | Baust et al. |
| 2012/0029493 A1 | 2/2012 | Wittenberger et al. |
| 2012/0157968 A1* | 6/2012 | Eldredge ............... A61M 15/08 604/514 |
| 2012/0197245 A1 | 8/2012 | Burnett |
| 2013/0006326 A1 | 1/2013 | Ackermann et al. |
| 2013/0018366 A1 | 1/2013 | Wu et al. |
| 2013/0211415 A1* | 8/2013 | Zerfas ................ A61B 17/00234 606/114 |
| 2013/0218151 A1 | 8/2013 | Mihalik et al. |
| 2013/0253387 A1 | 9/2013 | Bonutti et al. |
| 2013/0310822 A1 | 11/2013 | Mayse et al. |
| 2013/0345700 A1 | 12/2013 | Hlavka et al. |
| 2014/0058369 A1 | 2/2014 | Hon |
| 2014/0186341 A1 | 7/2014 | Mayse et al. |
| 2014/0207130 A1 | 7/2014 | Fourkas et al. |
| 2014/0228875 A1 | 8/2014 | Saadat et al. |
| 2014/0236148 A1 | 8/2014 | Hlavka et al. |
| 2014/0257271 A1 | 9/2014 | Mayse et al. |
| 2014/0276792 A1 | 9/2014 | Kaveckis et al. |
| 2014/0277429 A1 | 9/2014 | Kuzma et al. |
| 2014/0316310 A1 | 10/2014 | Ackermann et al. |
| 2014/0371812 A1 | 12/2014 | Ackermann et al. |
| 2015/0031946 A1 | 1/2015 | Saadat et al. |
| 2015/0045781 A1 | 2/2015 | Abboud et al. |
| 2015/0065810 A1* | 3/2015 | Edgren .................. A61B 17/24 600/249 |
| 2015/0080870 A1 | 3/2015 | Wittenberger |
| 2015/0119868 A1 | 4/2015 | Lalonde et al. |
| 2015/0126986 A1 | 5/2015 | Kelly et al. |
| 2015/0157382 A1 | 6/2015 | Avitall et al. |
| 2015/0164571 A1 | 6/2015 | Saadat |
| 2015/0190188 A1 | 7/2015 | Lalonde |
| 2015/0196345 A1 | 7/2015 | Newell et al. |
| 2015/0196740 A1 | 7/2015 | Mallin et al. |
| 2015/0223860 A1 | 8/2015 | Wittenberger et al. |
| 2015/0238754 A1 | 8/2015 | Loudin et al. |
| 2015/0250524 A1 | 9/2015 | Moriarty et al. |
| 2015/0265329 A1 | 9/2015 | Lalonde et al. |
| 2015/0265812 A1 | 9/2015 | Lalonde |
| 2015/0313661 A1 | 11/2015 | Wu et al. |
| 2016/0008058 A1* | 1/2016 | Hu .................... A61M 25/0147 606/21 |
| 2016/0022992 A1 | 1/2016 | Franke et al. |
| 2016/0038212 A1 | 2/2016 | Ryba et al. |
| 2016/0045277 A1 | 2/2016 | Lin et al. |
| 2016/0066975 A1 | 3/2016 | Fourkas et al. |
| 2016/0074090 A1 | 3/2016 | Lalonde et al. |
| 2016/0114163 A1 | 4/2016 | Loudin et al. |
| 2016/0114172 A1 | 4/2016 | Loudin et al. |
| 2016/0012118 A1 | 5/2016 | Franke et al. |
| 2016/0143683 A1 | 5/2016 | Aluru et al. |
| 2016/0158548 A1 | 6/2016 | Ackermann et al. |
| 2016/0166305 A1 | 6/2016 | Nash et al. |
| 2016/0166306 A1 | 6/2016 | Pageard |
| 2016/0220295 A1 | 8/2016 | Wittenberger |
| 2016/0287315 A1 | 10/2016 | Wolf et al. |
| 2016/0317794 A1 | 11/2016 | Saadat |
| 2016/0331433 A1 | 11/2016 | Wu et al. |
| 2016/0331459 A1* | 11/2016 | Townley .................. A61N 7/00 |
| 2016/0354134 A1 | 12/2016 | Pageard |
| 2016/0354135 A1 | 12/2016 | Saadat |
| 2016/0354136 A1 | 12/2016 | Saadat |
| 2016/0361112 A1 | 12/2016 | Wolf et al. |
| 2017/0007316 A1 | 1/2017 | Wolf et al. |
| 2017/0014258 A1 | 1/2017 | Wolf et al. |
| 2017/0042601 A1 | 2/2017 | Kim et al. |
| 2017/0056087 A1 | 3/2017 | Buckley et al. |
| 2017/0056632 A1 | 3/2017 | Jenkins et al. |
| 2017/0135723 A1* | 5/2017 | Zarembinski ...... A61M 25/0084 |

FOREIGN PATENT DOCUMENTS

| | | |
|---|---|---|
| EP | 2662046 | 11/2013 |
| EP | 2662116 | 11/2013 |
| WO | 99020185 | 4/1999 |
| WO | 9927862 | 6/1999 |
| WO | 99030655 | 6/1999 |
| WO | 0009053 | 2/2000 |
| WO | 0047118 | 8/2000 |
| WO | 0054684 | 9/2000 |
| WO | 0164145 | 9/2001 |
| WO | 01095819 | 12/2001 |
| WO | 0204042 | 1/2002 |
| WO | 0207628 | 4/2002 |
| WO | 02069862 | 9/2002 |
| WO | 0200128 | 11/2002 |
| WO | 02083196 | 2/2003 |
| WO | 03013653 | 2/2003 |
| WO | 03026719 | 4/2003 |
| WO | 03051214 | 6/2003 |
| WO | 03028524 | 10/2003 |
| WO | 03020334 | 12/2003 |
| WO | 03088857 | 12/2003 |
| WO | 2004000092 | 12/2003 |
| WO | 2005089853 | 11/2005 |
| WO | 2004108207 | 12/2005 |
| WO | 2006002337 | 1/2006 |
| WO | 2006118725 | 11/2006 |
| WO | 2006119615 | 11/2006 |
| WO | 2006124176 | 11/2006 |
| WO | 2006017073 | 4/2007 |

(56) References Cited

FOREIGN PATENT DOCUMENTS

| | | |
|---|---|---|
| WO | 2007145759 | 12/2007 |
| WO | 2008000065 | 1/2008 |
| WO | 2008042890 | 4/2008 |
| WO | 2008046183 | 4/2008 |
| WO | 2008051918 | 5/2008 |
| WO | 2008157042 | 12/2008 |
| WO | 2009114701 | 9/2009 |
| WO | 2009146372 | 12/2009 |
| WO | 2010081221 | 7/2010 |
| WO | 2010083281 | 7/2010 |
| WO | 2010111122 | 9/2010 |
| WO | 2011014812 | 2/2011 |
| WO | 2011091507 | 8/2011 |
| WO | 2011091508 | 8/2011 |
| WO | 2011091509 | 8/2011 |
| WO | 2011091533 | 8/2011 |
| WO | 2012012868 | 2/2012 |
| WO | 2012012869 | 2/2012 |
| WO | 2012015636 | 2/2012 |
| WO | 2012019156 | 2/2012 |
| WO | 2012051697 | 4/2012 |
| WO | 2012027641 | 5/2012 |
| WO | 2012058156 | 5/2012 |
| WO | 2012058159 | 5/2012 |
| WO | 2012058160 | 5/2012 |
| WO | 2012058161 | 5/2012 |
| WO | 2012058165 | 5/2012 |
| WO | 2012058167 | 5/2012 |
| WO | 2012174161 | 12/2012 |
| WO | 2013035192 | 3/2013 |
| WO | 2013110156 | 8/2013 |
| WO | 2013155450 A1 | 10/2013 |
| WO | 2013173481 | 11/2013 |
| WO | 2013163325 | 2/2014 |
| WO | 2014113864 | 7/2014 |
| WO | 2014138866 | 9/2014 |
| WO | 2014138867 | 9/2014 |
| WO | 2015038523 | 3/2015 |
| WO | 2015048806 | 4/2015 |
| WO | 2015061883 | 5/2015 |
| WO | 2015081420 | 6/2015 |
| WO | 2015106335 | 7/2015 |
| WO | 2015114038 | 8/2015 |
| WO | 2015139117 | 9/2015 |
| WO | 2015139118 | 9/2015 |
| WO | 2015153696 | 10/2015 |
| WO | 2016183337 | 11/2016 |
| WO | 2016186964 | 11/2016 |
| WO | 2017034705 | 3/2017 |
| WO | 2017047543 | 3/2017 |
| WO | 2017047545 | 3/2017 |
| WO | 2017218854 | 12/2017 |

OTHER PUBLICATIONS

Bluestone et al., "Intranasal Freezing for Severe Epistaxis", Arch Otolaryng, vol. 85, Apr. 1967, 119-121.
Costa et al., "Radiographic and Anatomic Characterization of the Nasal Septal Swell Body", Arch Otolaryngol Head Neck Surg., vol. 136, No. 11, Nov. 2010, 1109.
Sanu , "Two Hundred Years of Controversy Between UK and USA", Rhinology, 86-91.
Settipane et al., "Update on Nonallergic Rhinitis", Annals of Allergy Asthma & Immunology, vol. 86, 2001, 494-508.
Arora et al., "Cryodestruction of Vidian Nerve Branches", Indian Journal of Otolaryngology, vol. 32, No. 3, Sep. 1980, pp. 80-82.
Bumsted , "Cryotherapy for Chronic Vasomotor Rhinitis: Technique and Patient Selection for Improved Results", Laryngoscope, vol. 94, Apr. 1984, pp. 539-544.
Girdhar-Gopal , "An Assessment of Postganglionic Cryoneurolysls for Managing Vasomotor Rhinitis", American Journal of Rhinology, vol. 8, No. 4,, Jul.-Aug. 1994, pp. 157-164.
Golhar et al., "The effect of Cryodestruction of Vidian Nasal Branches on Nasal Mucus Flow in Vasomotor Rhinitis", Indian Journal of Otolaryngology, vol. 33, No. 1, Mar. 1981, pp. 12-14.
Goode , "A Liquid Nitrogen Turbinate Probe for Hypertrophic Rhinitis", Arch Otolaryngol., vol. 103, 1977, p. 431.
Mehra et al., "Cryosurgery in Vasomotor Rhinitis—An Analysis of 156 Patients", Indian Journal of Otolaryngology, vol. 42, No. 3, Sep. 1990, pp. 95-98.
Ozenberger , "Cryosurgery for the Treatment of Chronic Rhinitis", Laryngoscope, vol. 83, No. 4, 1973, pp. 508-516.
Ozenberger , "Cryosurgery in Chronic Rhinitis", The Laryngoscope, vol. 80, No. 5, May 1970, pp. 723-734.
Principato , "Chronic Vasomotor Rhinitis: Cryogenic and Other Surgical Modes of Treatment", The Laryngoscope, vol. 89, 1979, pp. 619-638.
Rao , "Cryosurgery on Inferior turbinate hypertrophy under topical anaesthesia—is it boon in electricity deprived places", National Journal of Otorhinolaryngology and Head & Neck Surgery, vol. 1 (10), No. 1, Apr. 2013, pp. 7-9.
Saadat et al., U.S. Appl. No. 15/431,740, filed Feb. 13, 2017, "Method and Device for Image Guided Post-Nasal Nerve Ablation" 73 pages.
Strome , "A long-term assessment of cryotherapy for treating vasomotor instability", vol. 69, No. 12, http://apps.webofknowledge.com.laneproxy.stanford.edu/OutboundServic...marked_list_candidates=1&excludeEventConfig=ExcludeIfFromFullRecPage, Dec. 1990, pp. 839-842.
Terao et al., "Cryosurgery on Postganglionic Fibers (Posterior Nasal Branches) of the Pterygopalatine Ganglion for Vasomotor Rhinitis", Acta Otolaryngol., vol. 96, 1983, pp. 139-148.
European Search Report for corresponding European application No. 17814143.8, dated Feb. 6, 2020.

* cited by examiner

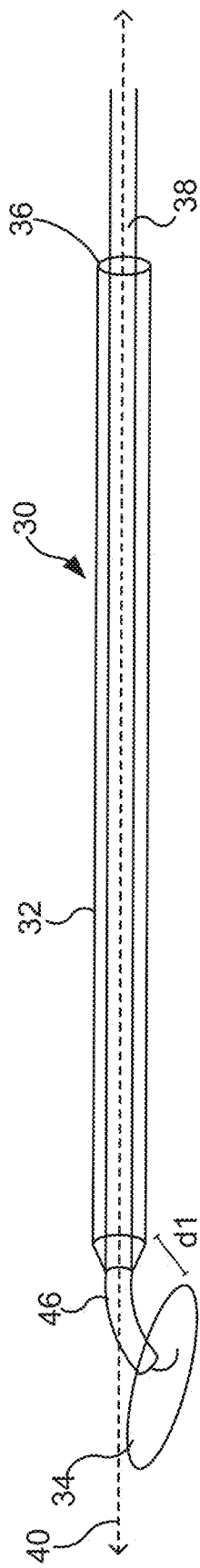
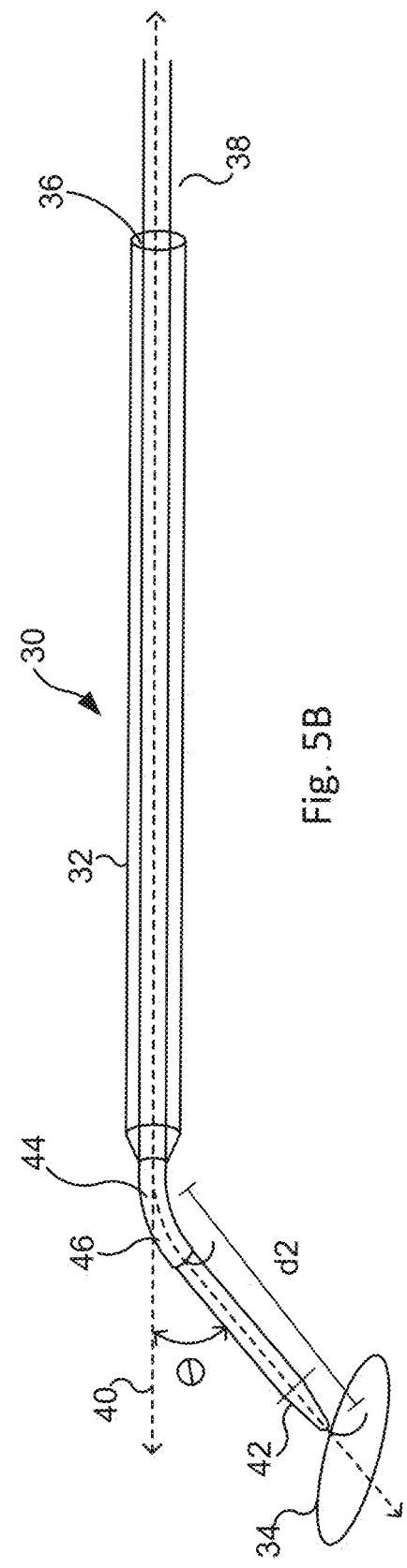
Fig. 5A
Fig. 5B

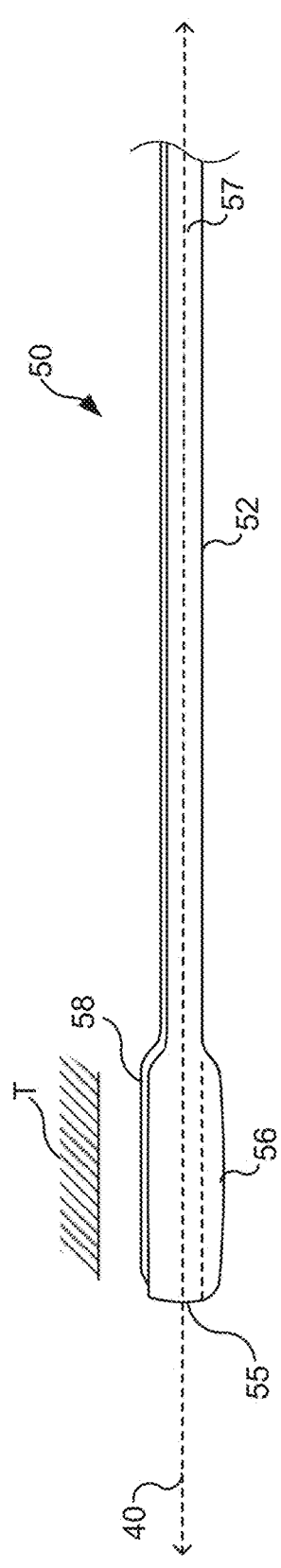
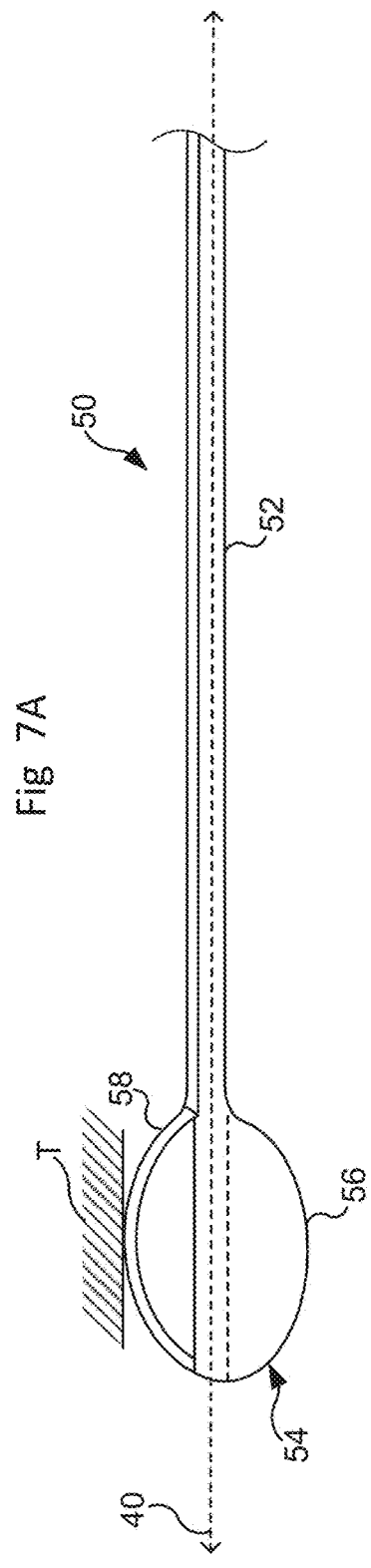
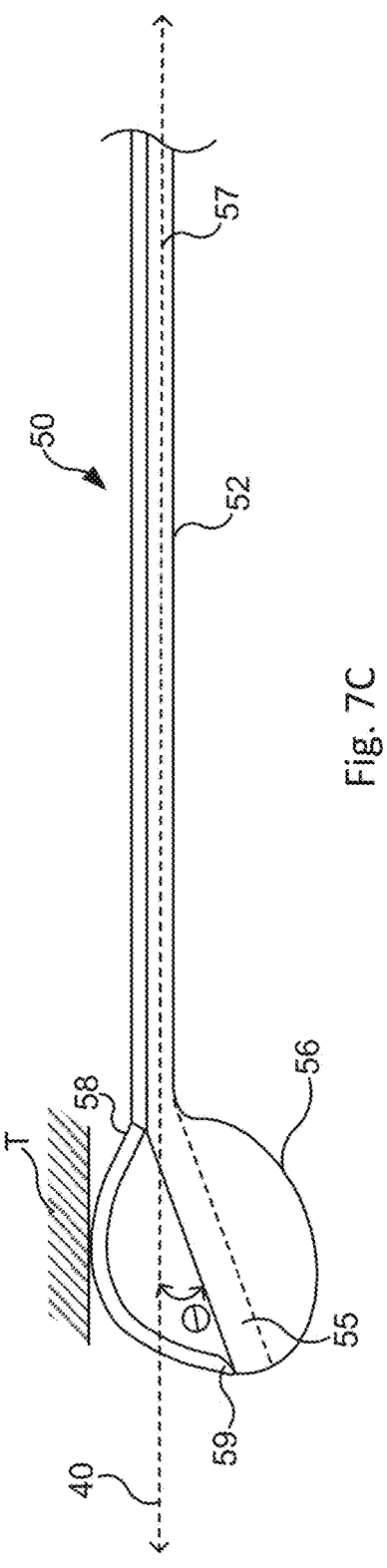
Fig. 7A
Fig. 7B
Fig. 7C

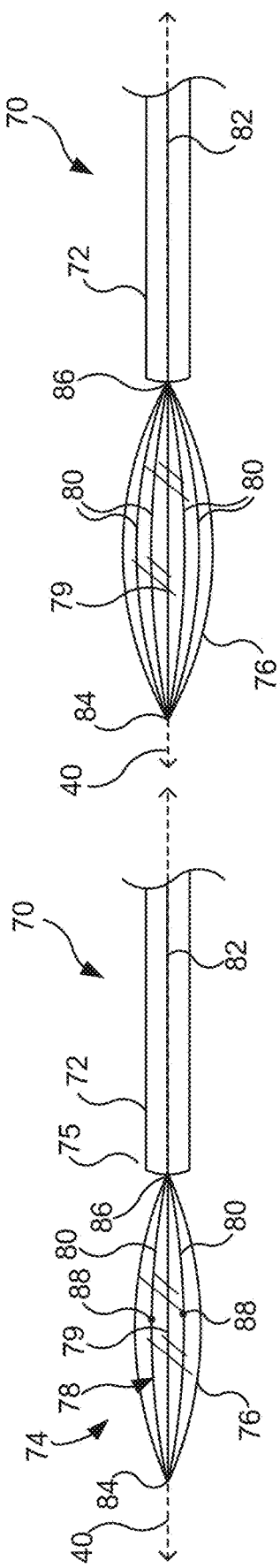
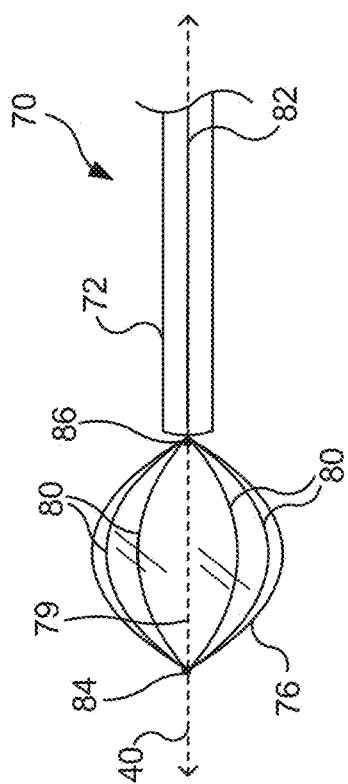
Fig. 11A
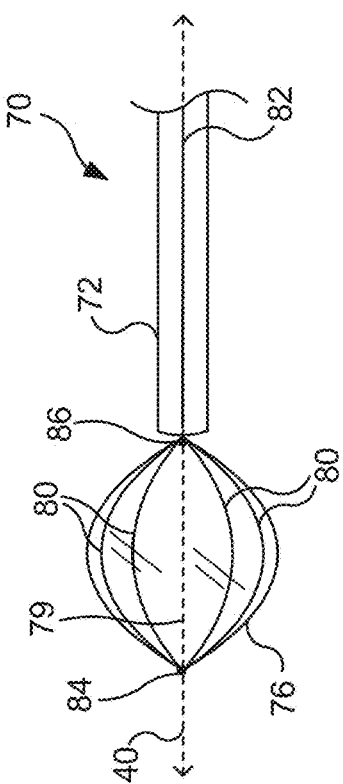
Fig. 11B
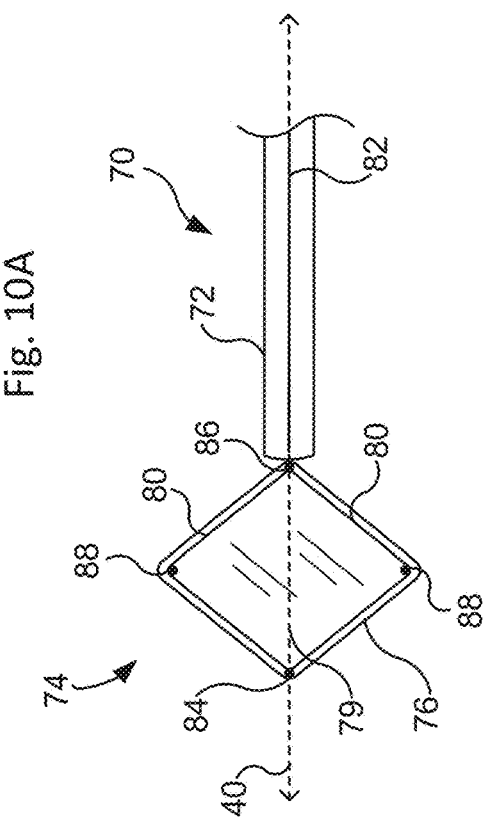
Fig. 10A
Fig. 10B

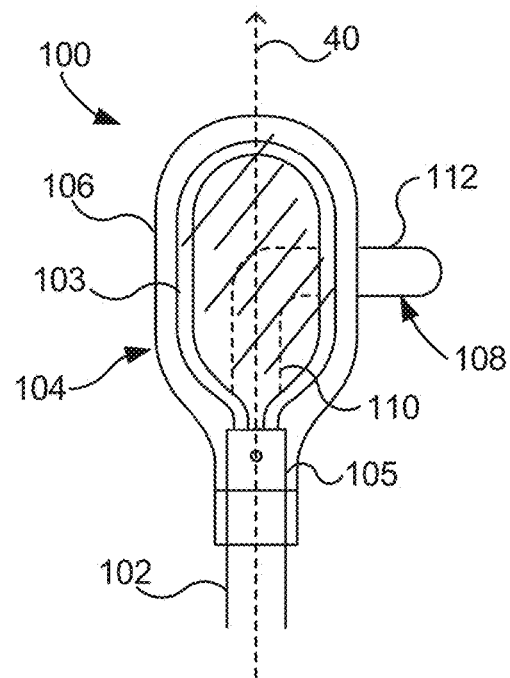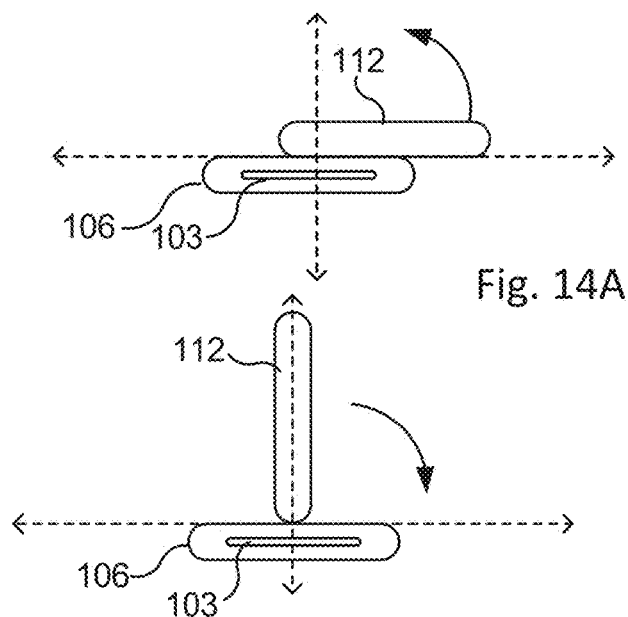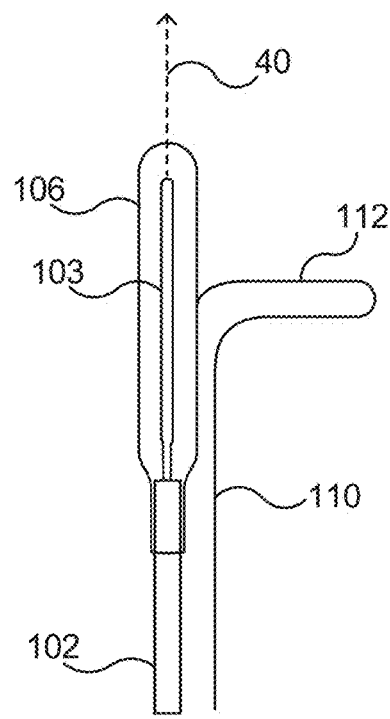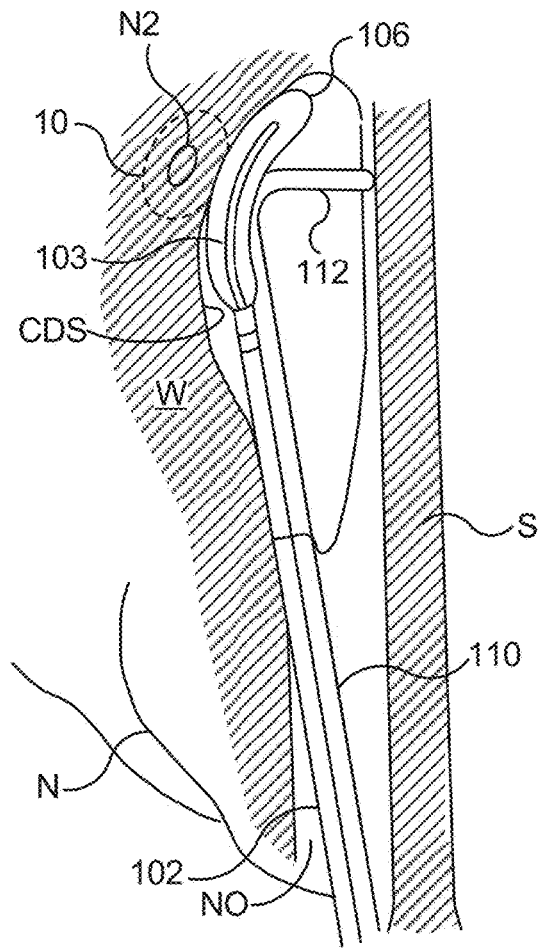
Fig 13
Fig. 14A
Fig. 14B
Fig. 15
Fig. 16

DEVICES AND METHODS FOR TREATING A LATERAL SURFACE OF A NASAL CAVITY

CROSS-REFERENCES TO RELATED APPLICATIONS

The present application claims the benefit of U.S. Provisional Patent Appln. No. 62/350,445 filed Jun. 15, 2016, entitled "DEVICES AND METHODS FOR TREATING A LATERAL SURFACE OF A NASAL CAVITY", the full disclosure of which is incorporated herein by reference in its entirety for all purposes.

BACKGROUND OF THE INVENTION

Referring to FIG. 1, the nose N provides a number of important features for the body shown on both sides of the sagittal plane SP of the body. Aside from the sense of smell, the nose provides an airway for respiration. The inspired air is warmed, filtered and humidified by the nasal mucosa as it passes through the nasal cavity. This supports the physiology of the respiratory tract and protects the lower airways from noxious stimuli in the environment. The airflow is regulated and modified by nasal turbinates T1, T2, T3. The nasal turbinates T1, T2, T3 are bony processes that extend inwardly from the lateral walls of the nose N toward the nasal septum S and are covered with mucosal tissue. There are three turbinates on each side of the nose N, the superior turbinate T1, the middle turbinate T2, and the inferior turbinate T3. Each turbinate defines a meatus, a natural body opening or passageway leading to the interior of the body. For example, the passageway between the superior turbinate T1 and the middle turbinate T2 is the superior meatus M1. This is the smallest meatus. The middle meatus M2 is a passageway that extends between the middle turbinate T2 and the inferior turbinate T3. The middle meatus M2 contains the semilunar hiatus, with openings or ostia leading into the maxillary, frontal, and anterior ethmoid sinuses. The passageway beneath the inferior turbinate T3 is the largest meatus, the inferior meatus M3 (not visible in FIG. 1). Ducts, known as the nasolacrimal ducts, drain tears from the eyes into the nose through openings located within the inferior meatus. These turbinates T1, T2, T3 serve to increase the interior surface area of the nose N and to impart warmth and moisture to air that is inhaled through the nose N. The mucosal tissue that covers the turbinates is capable of becoming engorged with blood and swelling, or becoming substantially devoid of blood and shrinking, in response to changes in physiologic or environmental conditions. This shrinking and swelling of the turbinates modifies the airflow from laminar to very turbulent. Turbulent air will spend more time in the nose as it passes through being filtered, humidified and warmed. This process requires the proper function of multiple systems, including the mucosal vasculature, autonomic nerves and sensory nerves.

FIG. 2 is an internal view of the nasal cavity of the nose of FIG. 1 showing the nasal structures and a portion of the nasal neural anatomy. Shown for orientation is the lateral nasal cavity wall W, the nose N, nostril NO, and the upper lip UL. The superior turbinate T1, middle turbinate T2, and inferior turbinate T3 are depicted along with a portion of the nasal neural anatomy shown in dashed lines. The sphenopalatine ganglion SG (also known as the pterygopalatine ganglion, Meckel's ganglion, or nasal ganglion) is a parasympathetic ganglion located within the lateral wall W beneath a portion of the middle turbinate M2. Extending from the sphenopalatine ganglion SG are the posterior nasal nerves. The lateral branches, known as the lateral posterior nasal nerves N1, N2 and N3 innervate the lateral walls and turbinates T1, T2, T3. The medial branches, known as the medial posterior nasal nerves, innervate the septum and are not shown in this figure. These nerves, along with the vasculature and various other nasal structures, assist in controlling the response of the mucosa to various factors, thereby influencing the shrinking and swelling of the turbinates and the production of nasal secretion. Ideally these systems maintain a properly functioning nasal environment, however there are a variety of factors which can lead to debilitated states, including rhinitis.

Rhinitis is defined as inflammation of the mucous membranes or mucosa lining the nose, characterized by nasal symptoms including itching, rhinorrhea, congestion, sneezing, and post-nasal drip. Rhinitis can occur due to the common cold or seasonal allergies. However, in some instances persistent or chronic rhinitis occurs wherein the symptoms continue long-term. Typically, the symptoms are present for some part of the day on most days over a long period of time. Many people become distressed by their regular, daily symptoms. Severe symptoms can affect their work, school, home and social life.

Chronic rhinitis is categorized into three types (1) non-allergic (vasomotor) rhinitis which includes idiopathic, hormonal, atrophic, occupational, and gustatory rhinitis, as well as rhinitis medicamentosa (drug-induced); (2) allergic rhinitis, triggered by pollen, mold, animal dander, dust, and other inhaled allergens; and (3) mixed rhinitis which is a combination of non-allergic and allergic rhinitis.

Non-allergic rhinitis refers to rhinitis that is not due to an allergy. The exact cause of non-allergic rhinitis is unknown however it can occur when blood vessels in the nose expand or dilate, filling the nasal lining with blood and fluid. There are several possible causes of this abnormal expansion of the blood vessels or inflammation in the nose. One possibility is that the nerve endings in the nose may be hyperresponsive to stimuli or triggers. There are a number common triggers of non-allergic rhinitis, including: (a) environmental or occupational irritants, such as dust, smog, secondhand smoke or strong odors (e.g. perfumes); (b) chemical fumes, such as exposure in certain occupations; (c) weather changes, such as temperature or humidity changes; (d) foods and beverages, such as hot or spicy foods or drinking alcoholic beverages; (e) certain medications, such as aspirin, ibuprofen (Advil, Motrin IB, others), high blood pressure medications (e.g. beta blockers), sedatives, antidepressants, oral contraceptives, drugs used to treat erectile dysfunction, and overuse of decongestant nasal sprays, and (f) hormone changes, such as due to pregnancy, menstruation, oral contraceptive use or other hormonal conditions such as hypothyroidism. Often these triggers are difficult or impossible to avoid leading to a chronic health condition.

Allergic rhinitis may follow when an allergen such as pollen or dust is inhaled by an individual with a sensitized immune system, triggering antibody production. These antibodies mostly bind to mast cells, which contain histamine. When the mast cells are stimulated by an allergen, histamine (and other chemicals) are released. This causes itching, swelling, and mucus production. Characteristic physical findings in individuals who have allergic rhinitis include conjunctival swelling and erythema, eyelid swelling, lower eyelid venous stasis, lateral crease on the nose, swollen nasal turbinates, and middle ear effusion. Allergic rhinitis can occur as a local allergy in the nose that is not revealed by intradermal or blood tests for allergies. Therefore, many people who were previously diagnosed with nonallergic rhinitis may actually have local allergic rhinitis.

Chronic rhinitis can lead to a variety of complications. Sinusitis is the most common complication of chronic rhinitis. The sinuses are small, air-filled spaces inside the cheekbones and forehead. Sinuses make some mucus which drains into the nose through small channels. If the nose is blocked or congested, the sinuses may not drain properly into the nose. This means that the mucus in the sinuses becomes blocked and can be more easily infected. Another complication is nasal polyps. These are soft, noncancerous (benign) growths that develop on the lining of the nose or sinuses due to chronic inflammation. Large polyps may block the airflow through the nose, making it difficult to breathe. Middle ear infections are another complication of chronic rhinitis due to the increased fluid and nasal congestion. Due to all of these, a common complication is decreased quality of life. Chronic rhinitis can be disruptive and interrupt daily activities. Productivity at work or school may lessen and time may be lost to symptom flares or doctor visits.

Medical treatments have been shown to have limited effects for chronic rhinitis sufferers. Allergic rhinitis sufferers are typically directed to avoid the cause of the allergy, which may be difficult or impossible, or use daily medications such as antihistamine nose sprays, antihistamine tablets and steroid nose sprays. These medications can be onerous and may cause undesired side effects. Non-allergic rhinitis is more difficult to treat and such treatment depends on the cause, which may be unknown. Therefore, chronic rhinitis sufferers typically have few treatment options.

One type of treatment is turbinate reduction surgery. As mentioned previously, the turbinates help warm and moisturize air as it flows through the nose. However, the turbinates become enlarged in chronic rhinitis, blocking nasal airflow. There are many ways to reduce the size of the turbinates. Surgery is typically called turbinate reduction or turbinate resection. It is important that the turbinate not be excessively reduced or removed completely because it can lead to "empty nose syndrome" (ENS) which describes a nose that has been physiologically crippled by excessive surgical removal of turbinates in the nose. Side effects include chronic mucosal inflammation (which can cause areas of the mucosa to atrophy), paradoxical obstruction (the feeling that the nose is stuffy, often accompanied by a constant or frequently occurring troubling feeling of suffocation generated by poor airflow feedback from the nasal mucosa), and neuropathic pain in the nose, pharynx, eustachian tube, throat, larynx, trachea, in more severe cases—in bronchi and lungs. Chronic hoarse voice and cough can also take place. This is caused by insufficiently processed (moisturized, warmed, cleaned) air passing through the respiratory system. ENS can also serve as a prerequisite for asthma.

Even when turbinate reduction surgery is done conservatively, it can have a temporary duration of effect of 1-2 years and can result in complications including mucosal sloughing, acute pain and swelling, and bone damage. Additionally, turbinate reduction does not treat the symptom of rhinorrhea.

In addition, some rhinitis patients are unresponsive to treatment. Such patients have failed treatments including antihistamines, topical and systemic steroids, topical anticholinergics, turbinectomies and specific immunotherapy (SIT), including subcutaneous (SCIT) and sublinguale (SLIT). For such patients, neural surgery has been introduced as a last line of treatment. Golding-Wood first introduced the concept of vidian neurectomy as definitive surgical management for chronic rhinitis in the 1960s. The theoretical basis of this surgery is an imbalance between parasympathetic and sympathetic innervation of the nasal cavity, and the resultant stimulation of goblet cells and mucous glands. The aim of this surgical technique is to disrupt this imbalance and reduce nasal secretions. The vidian nerve connects to the pterygopalatine ganglion inside pterygopalatine fossa and exits the skull through the pterygoid (vidian) canal. In a vidian neurectomy procedure, the vidian nerve was transected to decrease congestion and rhinitis. However, many practitioners have abandoned vidian neurectomy due to technical difficulty, its transient effectiveness and reports of complications, such as transient cheek and dental numbness, damage to the maxillary nerve (foramen rotundum), nasal crusting, dryness, initiation of bronchial asthma, bleeding, and ocular complications including vision loss and dry eyes due to severing of autonomic fibers in the vidian nerve that supply the lacrimal glands.

Recent studies have shown that selectively interrupting the Posterior Nasal Nerves (PNN) in patients with chronic rhinitis improves their symptoms while avoiding the morbidities associated with vidian neurectomy. Posterior nasal neurectomy, initially developed by Kikawada in 1998 and later modified by Kawamura and Kubo, is an alternative method in which neural bundles are selectively cut or cauterized from the sphenopalatine foramen. Autonomic and sensory nerve fibers that pass through the foramen anatomically branch into the middle and inferior turbinate and are distributed around the mucosal layer of the nose. Therefore, selective neurectomy at this point enables physicians to theoretically avoid detrimental surgical complications such as inhibition of lacrimal secretion.

The study by Ikeda et. al suggests that the effect of an anticholinergic drug on nasal symptoms resembled that of PNN resection in patients with chronic rhinitis. Based on his study the glandular mucosal acinar cells were significantly reduced after the PNN resection. The reduction in glandular cells may be explained by decreased secretion of the nerve growth factor or epidermal growth factor regulated by acetylcholine, a major neurotransmitter of parasympathetic systems.

Chronic rhinitis is a global medical problem with few successful treatment options having minimal side effects and satisfactory results. Some estimate between 10% and 25% of the world population suffers from rhinitis symptoms. That is roughly the population of the United States and China combined. Treatment tends to be expensive to our health care system. It is estimated in 2002 that allergic rhinitis alone accounted for 11 billion dollars in indirect and direct medical costs. The addition of non-allergic rhinitis grows this number substantially. Rhinitis is also a particular problem because patients can be misdiagnosed and mismanaged by primary care providers, costing much more to the system in lost days of work for ineffective treatment and continued discomfort to the patient. It is important to treat these patients properly in order to decrease the associated costs. At least some of these objectives will be met by the present invention.

BRIEF SUMMARY OF THE INVENTION

The present invention generally relates to medical systems, devices and methods, and more particularly relates to treating a tissue region within a nasal cavity of a patient. The invention allows for increased lateral contact or apposition of a target tissue region having at least one posterior nasal nerve with the end effector surface by lateral and/or longitudinal translation of the end effector relative to the surgical probe shaft. This improved lateral surface contact has several benefits, including improved patient outcomes and patient safety as the end effector is adequately in contact with target tissue for subsequent ablation therapy.

Embodiments include a method for treating a tissue region within a nasal cavity of a patient. The method includes inserting a distal end of a surgical probe into a nostril of a nasal cavity of a patient in a first configuration. The surgical probe includes an outer shaft, an inner shaft positioned within a lumen of the outer shaft and translatable relative to the outer shaft, and an end effector coupled to a distal end of the inner shaft. The distal portion of the inner shaft in the first configuration may be substantially aligned with a longitudinal axis of the outer shaft and the end effector may be positioned a first distance from a distal end of the outer shaft in the first configuration. The method further includes advancing the distal end of the surgical probe from the nostril into a middle meatus of the nasal cavity with the surgical probe in the first configuration. The method further includes translating the inner shaft relative to the outer shaft so that the surgical probe is deployed to a second configuration. In the second configuration, the end effector is translated longitudinally to a second distance greater than the first distance away from the distal end of the outer shaft and laterally away from the longitudinal axis of the outer shaft. In the second configuration, the end effector may be positioned within proximity of a tissue region having at least one posterior nasal nerve. The method further includes ablating the at least one posterior nasal nerve of the tissue region with the end effector.

In embodiments, the method includes initially contacting the end effector with an anatomical feature of the middle meatus to a lateral wall of the nasal cavity prior to translating the inner shaft relative to the outer shaft. Translating the inner shaft relative to the outer shaft may include translating from a posterior portion of the tissue region to an anterior portion of the tissue region so that a surface of the end effector successively increases lateral contact with the tissue region. This ability to fully contact the tissue region with the end effector using translation of the probe is advantageous because it can be accomplished without stretching the nostril or applying pressure to the septum. In embodiments, the first distance of the end effector from the distal end of the outer shaft may be in a range less than 10 mm and the second distance of the end effector from the distal end of the outer shaft may be in a range from 5 mm to 20 mm. The lateral translation of the end effector away from the longitudinal axis of the outer shaft may be in a range from 10 degrees to 90 degrees.

In embodiments, the outer shaft may comprise an angled tip defining an angle between the distal portion of the inner shaft in the second configuration and the longitudinal axis of the outer shaft. The probe may have an angled tip, biased stylet, or both features to articulate the end effector laterally away from the longitudinal axis of the outer shaft. The inner shaft may include a flexible or self-expandable material.

The inner shaft may include a biased stylet. Translating the biased stylet relative to the outer shaft may deploy the surgical probe from the first configuration where the stylet is constrained by the outer shaft in a substantially straightened configuration to the second configuration where the stylet is unconstrained by the outer shaft in a curved configuration to articulate the end effector laterally away from the longitudinal axis of the of the outer shaft.

The method may further include maintaining the outer shaft substantially stationary relative to the nostril during the translation of the inner shaft relative to the outer shaft. By maintaining the outer shaft in this way, as opposed to retreating out of the nostril with the outer shaft during translation, the translation of the inner shaft causes the end effector in laterally contact the tissue region. With this method nostril stretching by the outer shaft may be inhibited during the translation of the inner shaft relative to the outer shaft. The method may further include maintaining the outer shaft at an orientation substantially parallel to a sagittal plane of the patient during the translation of the inner shaft relative to the outer shaft.

In embodiments, the end effector may include an expandable structure coupled to the distal end of the inner shaft and an inner member is disposed at the distal end of the inner shaft extending within the expandable structure which encloses the inner member such that the inner member is unattached to an interior of the expandable structure. The method may further include introducing a cryogenic fluid into the expandable structure such that the expandable structure inflates from a deflated configuration into an expanded configuration against the tissue region. the cryogenic fluid may evaporate within the expandable structure so as to cryogenically ablate the at least one posterior nasal nerve. The method may further include maintaining the inner member against the interior of the expandable structure and the tissue region until the at least one posterior nasal nerve is cryogenically ablated.

In embodiments, the inner member may include a first member and a second member. The inner member may be configurable from an expanded configuration wherein the first member and second member define a first width of the end effector between the first member and the second member, to a compressed configuration wherein the first member and the second member define a second width of the end effector that is smaller than the first width. The inner member may be in the compressed configuration when the distal end of the surgical probe is inserted into the nostril and in the expanded configuration when the end effector is positioned within the tissue region having the at least one posterior nasal nerve. The first width may be in a range from 10 mm to 20 mm. The first member and second member do not overlap in the expanded configuration. The second width may be in a range from 5 mm to 19 mm. The first member and second member may overlap in the compressed configuration. The first and second members may have a heart shape in the expanded configuration and an oblong shape in the compressed configuration. The inner member may include a planar member having an elongate loop shape.

Embodiments further include a telescoping surgical probe, which may be used in the methods discussed above for treating a tissue region within a nasal cavity of a patient. The probe may include an elongate outer shaft having a distal end configured for insertion into a nostril of a nasal cavity of a patient. The outer shaft has a longitudinal axis and lumen therethrough. The probe may further include an elongate inner shaft positioned within the lumen of the outer shaft and translatable relative to the outer shaft and an end effector coupled to a distal end of the inner shaft. The distal portion of the inner shaft may be substantially aligned with the longitudinal axis of the outer shaft and the end effector may be positioned a first distance from the distal end of the outer shaft when the surgical probe is in a first configuration during insertion and advancement of the surgical probe into a middle meatus of the nasal cavity. Translation of the inner shaft relative to the outer shaft may configure the end effector longitudinally to a second distance greater than the first distance away from the distal end of the outer shaft and laterally away from the longitudinal axis of the outer shaft when the surgical probe is in a second configuration, wherein the end effector in the second configuration is in lateral contact with a tissue region having at least one posterior nasal nerve and is configured to ablate the at least one posterior nasal nerve. The end effector may include a cryotherapy balloon; and the probe may further include a cryogenic fluid source coupled to the inner shaft and a lumen disposed in the inner shaft and in fluid communication with the cryogenic fluid source and an interior of the balloon. Further, the end effector may be flexibly coupled to the inner shaft.

Further embodiments may include a probe for treating a target area within a nasal cavity. The probe may include an elongate probe shaft having a distal end configured for insertion into the nasal cavity, wherein the elongate shaft has a longitudinal axis and a lumen therethrough. The probe many further include a stylet comprising a shaft having a distal end and an end effector disposed along the distal end of the stylet shaft. The end effector may be configured to modify a property of the target area. The stylet shaft may have a curvature disposed proximal to the end effector. The distal end of the stylet may be retractable into the lumen of the probe shaft so that the lumen straightens the curvature of the stylet so as to position the end effector near the longitudinal axis and the distal end of the stylet is advanceable so that the curvature is positionable beyond the elongate probe shaft allowing the stylet to bend along the curvature so as to position the end effector laterally away from the longitudinal axis and toward the target area.

In embodiments, the target area may be located along a lateral wall of the nasal cavity and may include a posterior nasal nerve within a cul-de-sac. The curvature of the stylet may bend the stylet so that the end effector is positionable against the target area while the probe shaft extends out of a nostril without substantially tilting the probe shaft within the nostril. The curvature may bend the stylet so that the end effector is positionable against the lateral wall while the probe shaft extends out of a nostril, and wherein an application of force along the longitudinal axis of the probe shaft translates the force to lateral pressure applied by the end effector to the target area. The curvature may bend the stylet approximately 10-80 degrees from the longitudinal axis.

In embodiments, the temperature therapy is cryotherapy and the end effector may comprise a balloon. The end effector may be flexibly joined with the shaft of the stylet.

Further embodiments may include a probe for treating a target area located within a nasal cavity. The target area may be disposed lateral to an axis extending through a nostril. The probe may include a probe shaft having a distal end configured for insertion into the nasal cavity and a longitudinal axis alignable with the axis extending through the nostril. The probe may further include an end effector disposed along the distal end of the probe shaft, and the end effector may be configured to contact the target area while the longitudinal axis is aligned with the axis extending through the nostril. The probe may further include a lateral support disposed along the distal end of the probe shaft, wherein a portion of the lateral support is moveable laterally outwardly from the longitudinal axis so as to contact a support surface within the nasal cavity so as to hold the end effector against the target area. The target area may be located along a lateral wall of the nasal cavity and the support surface may be located along a turbinate or septum. The target area may include a posterior nasal nerve within a cul-de-sac. The end effector may be disposed along a first side of the distal end of the probe shaft and the lateral support may be disposed along a second side of the distal end of the probe shaft, wherein the lateral support is movable between a collapsed configuration wherein the support is disposed near the longitudinal axis during insertion into the nasal cavity and an expanded configuration wherein the portion of the lateral support moves laterally outwardly. The lateral support may include a flexible strip fixedly attached to the elongate probe shaft near the distal end of the probe shaft and slidably attached to the probe shaft at a proximal location so that sliding advancement of the flexible strip in relation to the probe shaft causes the lateral support to move from the collapsed configuration to the expanded configuration. The strip may bow laterally outwardly from the probe shaft between the fixed attachment and the slidable attachment when in the expanded configuration. A portion of the support may contact the support surface within the nasal cavity so as to hold the end effector against the target area with sufficient force to apply pressure to the target area. A portion of the lateral support may be extendable laterally outwardly so as to contact the support surface within the nasal cavity with sufficient force to tip a portion of the distal end of the probe shaft away from the longitudinal axis.

In embodiments, the lateral support may have a free end which extends laterally outwardly from the longitudinal axis so as to contact the support surface to provide lateral support to the end effector. The free end may extend laterally outwardly from the longitudinal axis by bending at a hinge, kink point or pre-formed bend. The lateral support may include a strip slidably attached to the probe shaft so that sliding advancement of the strip in relation to the probe shaft releases the free end and allows the free end to bend laterally outwardly. The end effector may include a sheath, and the lateral support may include an internal expander disposed within the sheath. The expander may have a longitudinal segment aligned with the longitudinal axis and at least one expanding segment, and the expander may be movable between a collapsed configuration wherein the at least one expanding segment is disposed near the longitudinal segment and an expanded configuration wherein the at least one expanding segment moves laterally outwardly from the longitudinal axis. The sheath may include a non-inflatable balloon configured to delivery cryotherapy. The at least one expanding segment may include at least two expanding segments, and one of the at least two expanding segments may expand laterally outwardly toward the target area while another of the at least two expanding segments expands laterally outwardly toward the surface within the nasal cavity. At least one of the at least one expanding segments may move laterally outwardly from the longitudinal axis by flexible bowing. At least one of the at least one expanding segments may move laterally outwardly from the longitudinal axis by bending at a hinge, kink point or flex point. At least one expanding segments may be fixedly attached to the longitudinal segment at a first location and slidably attached at a second location, and retraction of the longitudinal segment may draw the first location toward the second location which causes the at least one expanding segment to expand laterally outwardly.

Further embodiments may include a probe for treating a target area within a nasal cavity. The probe may include an elongate probe shaft having a longitudinal axis and a distal end configured for insertion into the nasal cavity. The probe may further include an end effector disposed along a first side of the distal end of the probe shaft, and the end effector may be configured for temperature therapy of the target area.

The probe may further include a lateral support disposed along a second side of the distal end of the probe shaft. The lateral support may be movable between a collapsed configuration wherein the support is disposed near the longitudinal axis during insertion into the nasal cavity and an expanded configuration wherein a portion of the support extends laterally outwardly from the longitudinal axis so as to contact a surface near the target area to provide lateral support to the end effector.

The target area may be located along a lateral wall of the nasal cavity and the surface is located along a turbinate or septum. The target area may include a posterior nasal nerve within a cul-de-sac. The first side and the second side of the distal end of the probe shaft may be on opposite sides of the distal end of the support probe. The temperature therapy may include cryotherapy.

The lateral support may include a flexible strip fixedly attached to the elongate probe shaft near the distal end of the probe shaft and slidably attached to the probe shaft at a proximal location so that sliding advancement of the flexible strip in relation to the probe shaft causes the lateral support to move from the collapsed configuration to the expanded configuration. The strip may bow laterally outwardly from the probe shaft between the fixed attachment and the slidable attachment when in the expanded configuration. A portion of the support may be extendable laterally outwardly so as to contact the surface near the target area with sufficient force to translate pressure to the end effector against the target area. A portion of the support may be extendable laterally outwardly so as to contact the surface near the target area with sufficient force to tip a portion of the distal end of the probe shaft away from the longitudinal axis. The lateral support may have a free end which extends laterally outwardly from the longitudinal axis so as to contact the surface near the target area to provide lateral support to the end effector. The lateral support may have a free end which extends laterally outwardly from the longitudinal axis by bending at a hinge, kink point or pre-formed bend. The lateral support may include a strip slidably attached to the probe shaft so that sliding advancement of the strip in relation to the probe shaft releases the free end and allows the free end to bend laterally outwardly.

Further embodiments may include a probe for treating a target area within a nasal cavity. The probe may include an elongate probe shaft having a longitudinal axis and a distal end configured for insertion into the nasal cavity. The probe may further include a sheath disposed along the distal end of the probe shaft. The sheath may be configured to deliver temperature therapy to the area. The probe may further include an internal expander disposed within the sheath, wherein the expander has a longitudinal segment aligned with the longitudinal axis and at least one expanding segment, wherein the expander is movable between a collapsed configuration wherein the at least one expanding segment is disposed near the longitudinal segment during insertion into the nasal cavity and an expanded configuration wherein the at least one expanding segment moves laterally outwardly from the longitudinal axis so as to contact a surface near the target area to provide lateral support to the sheath. The sheath may comprise a non-inflatable balloon configured to delivery cryotherapy. The at least one expanding segment may comprise at least a two expanding segments, wherein one of the at least two expanding segments expands laterally outwardly toward the target area while another of the at least two expanding segments expands laterally outwardly toward a surface within the nasal cavity opposing the target area.

The target area may comprise a portion of a lateral wall containing a proximal nasal nerve and the surface within the nasal cavity opposing the target area comprises a turbinate or a septum. At least one of the at least one expanding segments may move laterally outwardly from the longitudinal axis by flexible bowing. At least one of the at least one expanding segments may move laterally outwardly from the longitudinal axis by bending at a hinge, kink point or flex point. At least one expanding segment may be fixedly attached to the longitudinal segment at a first location and slidably attached at a second location, and the retraction of the longitudinal segment may draw the first location toward the second location which causes the at least one expanding segment to expand laterally outwardly.

Further embodiments may include a probe for treating a target area within a nasal cavity. The probe may include an elongate probe shaft having a longitudinal axis and a distal end configured for insertion into the nasal cavity. The probe may further include an end effector disposed along the distal end of the probe shaft. The end effector may be configured to deliver therapy to the target area. The probe may further include an elongate rod having a proximal end alignable with the longitudinal axis of the elongate probe and a curved distal end extending laterally outwardly from the longitudinal axis. The distal end may have a tip positionable against a support surface within the nasal cavity, wherein positioning the tip against the support surface presses the end effector against the target area during delivery of therapy. The curved distal end may have a curvature of approximately 90 degrees so that the distal end of the rod is substantially perpendicular to the longitudinal axis. The rod may be malleable so as to adjust a curvature of the curved distal end. The end effector may have a broad surface configured to contact the target area, and the distal end of the rod may be rotatable between a position in parallel with the broad surface and perpendicular with the broad surface.

The target area may be located along a lateral wall of the nasal cavity and the support surface may be located along a turbinate or septum. The target area may include a posterior nasal nerve within a cul-de-sac.

The rod may be advanceable and retractable in relation to the probe shaft. The rod may be advanceable so that the curved distal end is positionable distal to the end effector and extends around the end effector so that the support surface that its distal tip is positionable against is adjacent the target area. The end effector may comprise an inflatable balloon and the rod may stabilize the balloon during delivery of the temperature therapy. The temperature therapy may include cryotherapy.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 5A-5B illustrate an embodiment of a probe that allows a therapeutic end effector to be moved laterally while the shaft maintains position.

FIGS. 7A-7B illustrate embodiments of a probe that provides lateral support to a therapeutic end effector.

FIG. 7C illustrates a probe wherein the lateral support is advanced so as to tip the distal end of the probe shaft.

FIGS. 10A-10B illustrates an embodiment of a probe having an internal expander.

FIGS. 11A-11B illustrate another embodiment of a probe having an internal expander.

FIGS. 13, 14A-14B, 15, 16 illustrate another embodiment of a probe that provides lateral support to the therapeutic end effector.

DETAILED DESCRIPTION OF THE INVENTION

Figure 1:
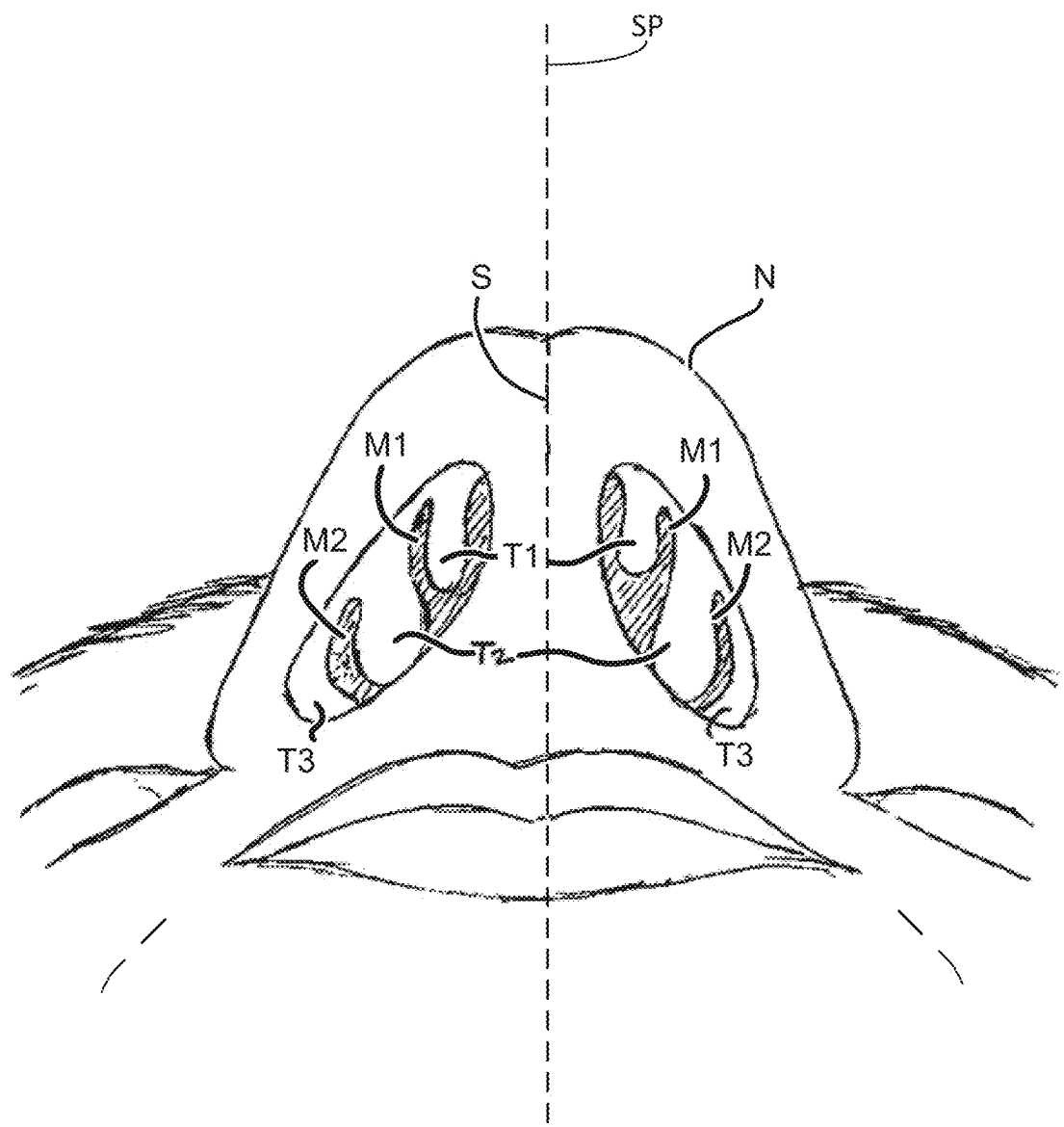
FIG. 1 provides an illustration of the anatomy of the nose.
Figure 2:
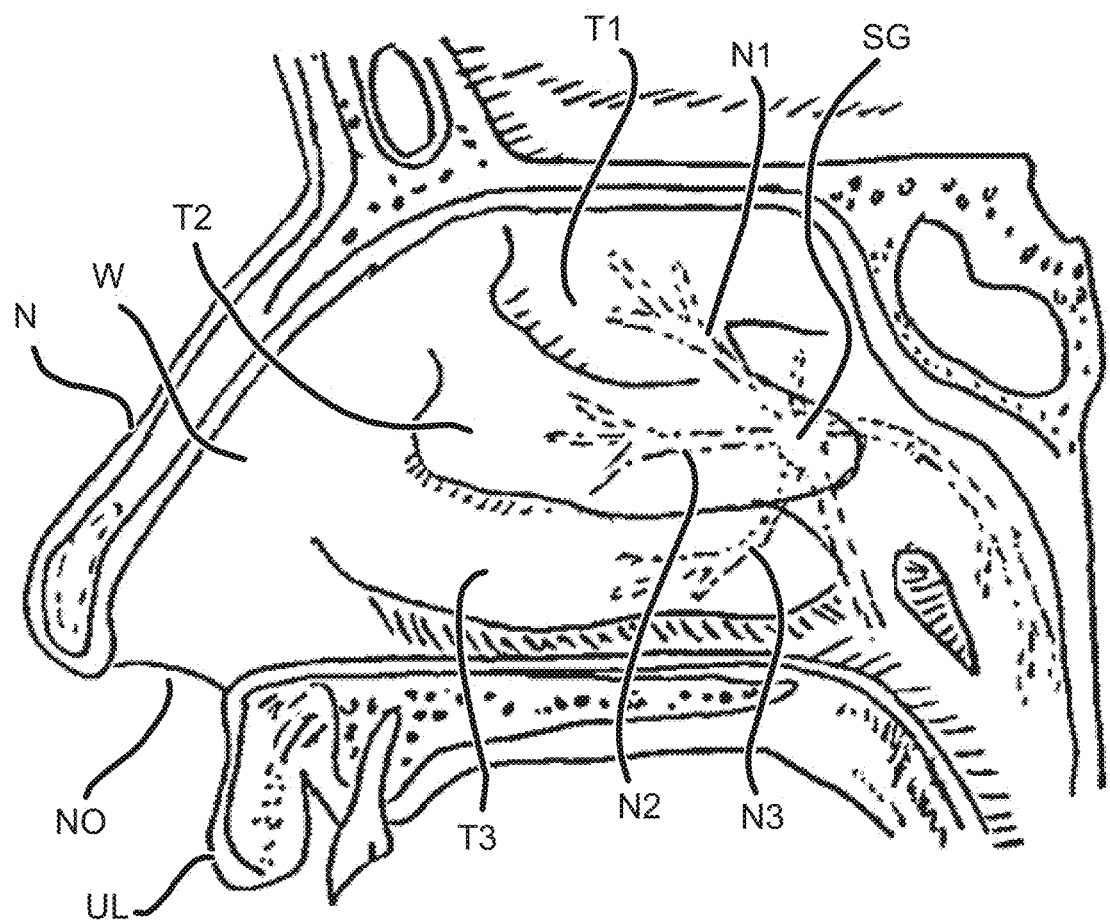
FIG. 2 provides an illustration of an internal view of the nose anatomy.
Figure 3:
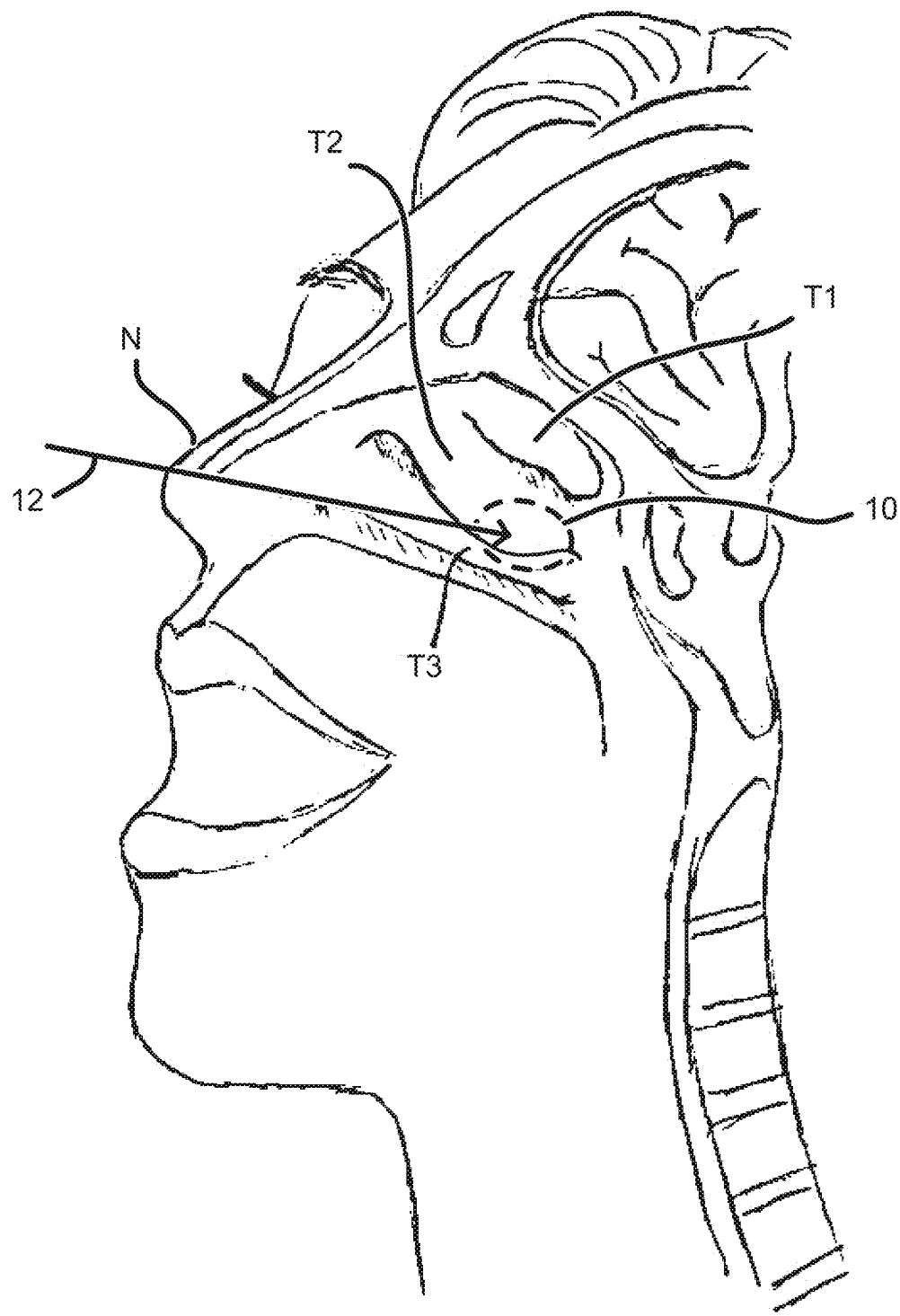
FIG. 3 illustrates a portion of the nasal cavity including a target treatment area.

The present invention generally relates to medical devices, systems and methods, and more particularly relates to devices, systems and methods that treat rhinitis. Such treatment of rhinitis is achieved by decreasing or interrupting nerve signals that are transmitted from the sphenopalatine ganglion to the nasal mucosa via the posterior nasal nerves. Decrease or interruption of nerve signals can be attained by a variety of methods, particularly by the application of physical therapies (compression or cutting), thermal therapies (heat or cold), or chemical therapies (alcohol or anesthetic injections). Examples of thermal therapies include cryotherapy, cryoneuromodulation, cryomodulation, cryolysis, cryoablation, and thermoablation. It has been found that a specific target area within the nasal cavity is particularly effective in treating rhinitis. This target area is located along the lateral wall W in the middle meatus within a cul-de-sac CDS. The cul-de-sac CDS in the middle meatus is defined superiorly by the Ethmoid bulla, posteriorly defined by the most posterior attachment point of the middle turbinate T2 to the lateral wall, inferiorly defined by the inferior turbinate T3 attachment to the lateral wall, anteriorly defined by the posterior tail of the uncinate process, and medially defined by the lateral side of the middle turbinate. The target area within the cul-de-sac may be approximately 177 mm$^2$ in area, and in embodiments may range from 13 mm$^2$ to 315 mm$^2$. The target area may include a concaved surface portion and a portion protruding out from the wall on the inferior side where the inferior turbinate attaches. FIG. 3 illustrates a portion of the nasal cavity including the target area 10. In this illustration, a portion of the left side of the patient's face is omitted to allow for viewing inside of the nasal cavity, in particular the septum and the left side of the nose N has been omitted. Thus, the superior, middle and inferior turbinates T1, T2, T3 of the right side of the face are visible along the lateral wall W. The arrow 12 indicates a straight pathway through the nostril NO toward the location of the target area 10.

Figure 4A:
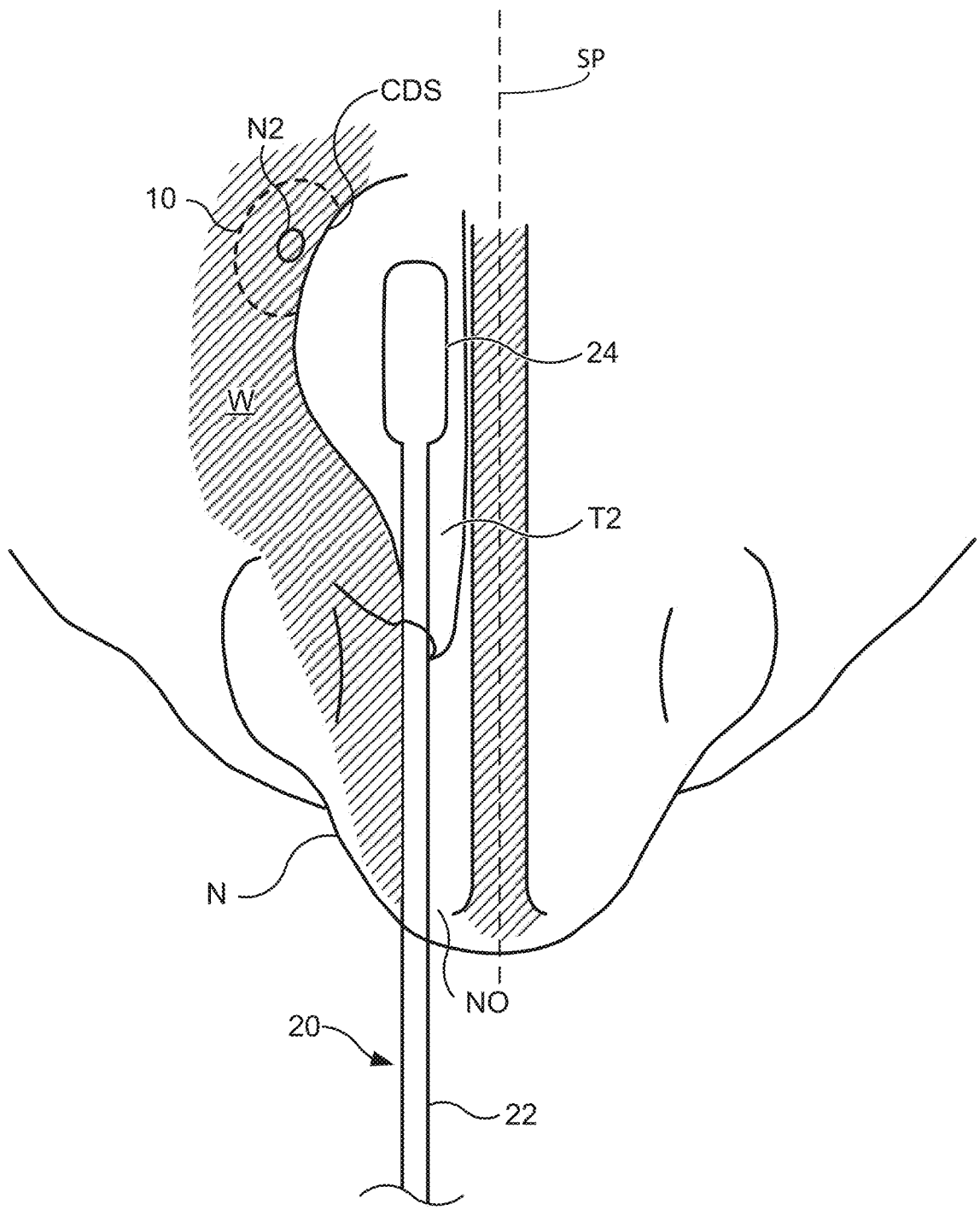
FIG. 4A illustrates a probe having a shaft and a therapeutic end effector inserted into a nostril of a nose.

FIG. 4A illustrates an embodiment of a probe 20 having a shaft 22 and a therapeutic end effector 24 inserted into the right nostril N and advanced into the middle meatus, an area underneath the middle turbinate and above the inferior turbinate, in a direction substantially corresponding to arrow 12 of FIG. 3. The portion of the nasal cavity shown in FIG. 4A is a cross-section from above. As shown, a portion of the lateral wall W at the target area 10 is concave. The lateral posterior nasal nerves N2 passes through lateral wall at the Sphenopalatine foramen located within or slightly above the middle turbinate attachment to the lateral wall W. Portions of the posterior nasal nerves N2 spread in the nasal cavity and innervate the mucosa along the lateral wall W of the cul-de-sac CDS, defining the target area 10. By applying one or more of the therapies noted above across the target area 10 with the end effector 24 of the probe 20, the parasympathetic nerve signals passing there through are decreased or interrupted which alleviates rhinitis symptoms. The position and contours of the target area 10 in the cul-de-sac CDS can impede contact of the therapeutic end effector 24 across the entire target area 10. Without contact across the entire target area the treatment may be less effective or ineffective. Therefore, it is desired to have complete contact with the target area within cul-de-sac CDS with the end effector 24 and apply pressure to the target area 10. Such application of pressure compresses and thins the tissue layer (nasal mucosa) between the nerve area N2 and the end effector 24, bringing the end effector 24 closer to the nerves and in cryoablation applications allows the temperature of the nerve to reach below –20 degrees Celsius. Such pressure may also reduce blood flow through the target area 10. Both of these aspects may increase the penetration and area of the therapy, increasing the effectiveness of the thermal therapy.

Figure 4B:
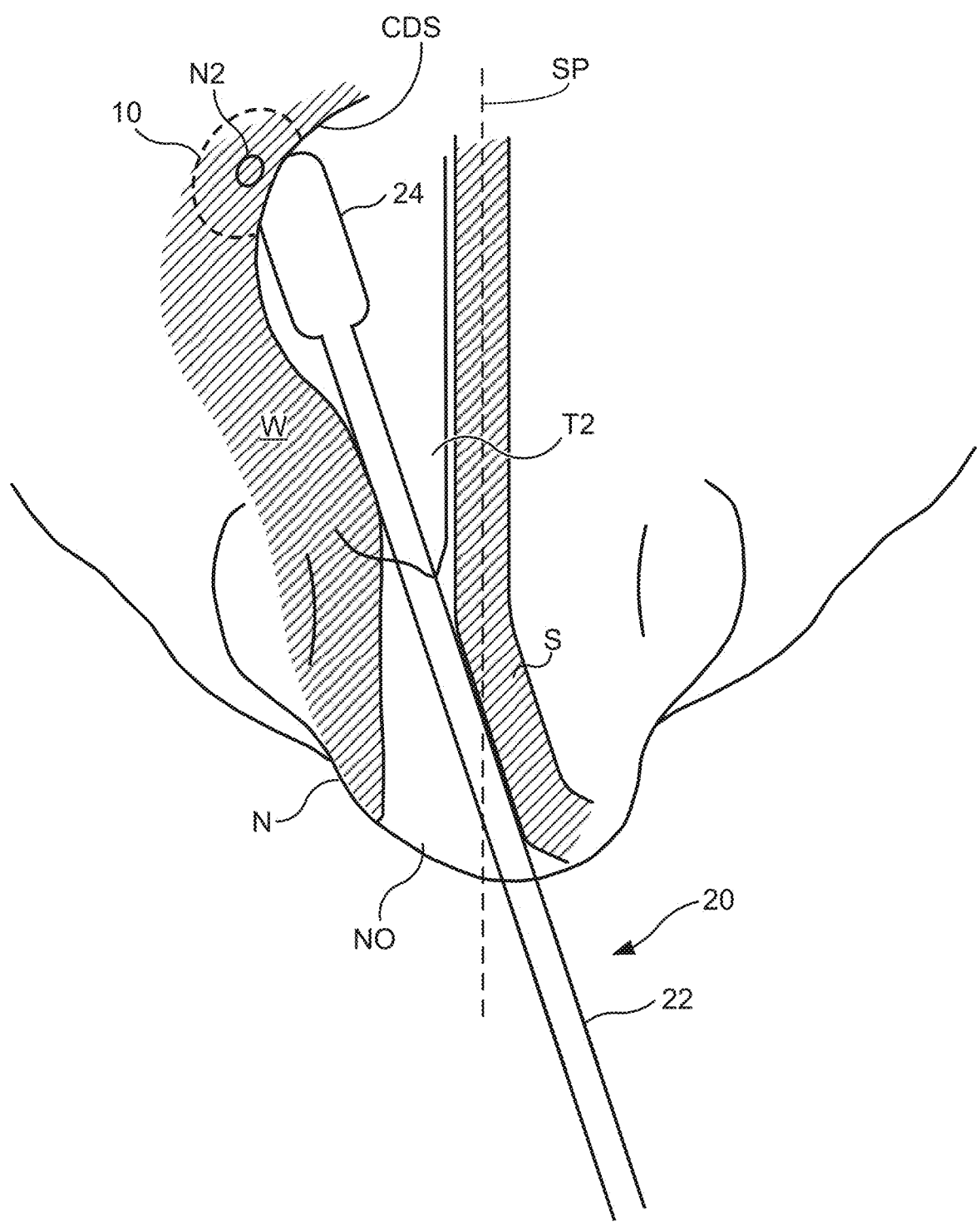
FIG. 4B illustrates the probe of FIG. 4A tilted within the nostril.

In embodiments, to make contact and apply pressure to the target area 10, the probe 20 may be angled laterally relative to the sagittal plane so that the end effector reaches over the inferior turbinate T3 and underneath the middle turbinate T2, as illustrated in FIG. 4B, so that the end effector 24 enters the cul-de-sac CDS and makes contact with the lateral wall W. As shown, an angle, relative to the sagittal plane SP, used to reach the target 10 with the end effector 24 may cause the shaft 22 of the probe 20 to press against the septum S and also stretch the nostril NO. This pressure against the septum and stretching of the nostril can be uncomfortable for and harmful to the patient. Further, the obstruction caused by the septum S, inferior turbinate T3 and nostril NO can limit the contact area of the end effector 24 and the amount of pressure that can be applied to the target area 10 and thereby limit the effectiveness of the therapy. In embodiments, the shaft 22 may include a bent portion so that the end effector 24 is offset from the longitudinal axis of the shaft 22. The bent portion may allow for more complete coverage of the target area 10 with the end effector 24. In embodiments, the bend makes the width of the probe 20 larger than a straight probe, and therefore in order to advance the bent probe through the nasal cavity into the middle meatus without causing patient discomfort from pressing into the turbinates and/or septum the shaft may be made of a flexible material. The flexible material may have elasticity and be able to be straighten when advanced into the nasal cavity without causing excessive pressure against the nostril and the septum. When the end effector reaches the middle meatus, the shaft will bias due to the elasticity of the material to return to the bent configuration. Returning to the bend configuration causes the end effector to translate laterally toward the target area and contact and apply pressure to the target area.

FIGS. 5A-5B show an embodiment of a probe 30 comprising an outer shaft 32 and an inner shaft 38, also referred to as a stylet. The inner shaft 38 is located within a lumen 36 of the outer shaft 32. The inner shaft 38 includes a distal end portion 42. Attached to the distal end portion is an end effector 34. The inner shaft 38 is able to translate within and relative to the outer shaft 32. Translation may be actuated with a trigger, or similar mechanism, located on a handle that the probe 30 is affixed to. The inner shaft 38 may translate from a first configuration, shown in FIG. 5A, wherein the end effector 34 is proximate to a distal end of the outer shaft 32, to a second configuration, as shown in FIG. 5B, wherein the end effector 34 is translated away from the distal end of the outer shaft 32. In the first configuration, the end effector 34 is positioned so that it substantially aligns with the longitudinal axis 40 of the outer shaft 32. For example, the end effector may not extend beyond 15 mm from the longitudinal axis in the first configuration. This allows for easy insertion into the nostril NO and advancement into a meatus, such as the middle meatus. As shown in FIG. 5B, in the second configuration, the end effector 34 is translated at an angle relative to the longitudinal axis 40 of the outer shaft 32 so that the end effector 34 moves away from the distal end of the outer shaft 32 both longitudinally and laterally.

The outer shaft 32 is sized and configured to be advanceable through a nostril NO of a patient and within the nasal cavity by a user outside of patient. In embodiments, the outer shaft 32 is 80 mm long or longer, 4 mm or less in diameter, and made of malleable or rigid material such as stainless steel or heat treated stainless steel. In embodiments, the outer shaft 32 is semi-malleable to rigid and has a substantially straight configuration extending along the straight longitudinal axis 40. The straightness of the outer shaft 32 allows the outer shaft 32 to reside comfortably within a nostril NO.

The end effector 34 is affixed to the distal end of the shaft 42. In embodiments, end effector 34 comprises a flexible inner member and a thin film outer member. The inner member can be made from stainless steel, nitinol, or a higher durometer plastic. The thin film outer member can be made from <0.005" thick polymer film. Film material can be nylon, LDPE, Urethane, PET or co-extrusions of these types. In cryoablation applications, the end effector may be designed to reach freezing temperatures on all surfaces of the thin film outer member. The lateral wall facing surface of the end effector has an area ranging 13-315 mm$^2$, with a preferred circular area of 177 mm$^2$. The end effector may be inflatable and the width between lateral wall facing surface and middle turbinate facing surface of the end effector 34 in a deflated state when advancing to the target area may be 0.2-1 mm. Once over the target area 10, the end effector may be transitioned to an inflated state with a width of 1 mm-10 mm. In embodiments, the lateral wall facing surface is a circular shape with a diameter of 15 mm. In embodiments, the end effector 34 is attached to the distal end portion 42 either in line with the longitudinal axis 44 of the distal end portion 42 or at an angle relative to the longitudinal axis 44 of the distal end portion 42.

In embodiments, the inner shaft 38, including the distal end portion 42, is comprised of a flexible material, such as a Nitinol, spring steel, Elgiloy or a flexible polymer. The inner shaft 38 may include a bend causing the distal end portion to be biased to a configuration where the distal end portion is at an angle relative to the rest of the inner shaft. The flexible material is configured to allow the distal end portion 42 and bend to straighten relative to the rest of the inner shaft 38, when the probe 30 is in the first configuration and the distal end portion 42 is positioned within the lumen 36 of outer shaft 32, as shown in FIG. 5A. In embodiments, the inner shaft 38 may be made of multiple components and/or materials. The distal end portion 42 may be made of a flexible material and the rest of the inner shaft 38 may be made of a semi-rigid to rigid material affixed to the distal end portion 42.

In embodiments, the distal end of the outer shaft includes an angled tip 46. The inner shaft 38 is advanced through the lumen 36 and the distal end portion 42 extends out of the outer shaft 32 through angled tip 46. Angled tip 46 includes a lumen directing inner shaft 38 out from the angled tip 46 at a desired angle relative to the longitudinal axis 40 of the outer shaft 32, as illustrated in FIG. 5B. In embodiments, the angle θ ranges from 10 to 90 degrees, more particularly from 20 to 70 degrees. The difference in distance the end effector 34 translates between the first configuration, at a distance of d1 from the distal end of the outer shaft, and the second configuration, at a distance of d2 from the distal end of the outer shaft, may ranges from 3 mm to 50 mm, and more particularly from 5 mm to 20 mm. During treatment, the range of translation may be based on the patient anatomy, and the inner shaft may be able to translate to any position with the range.

Figure 6A:
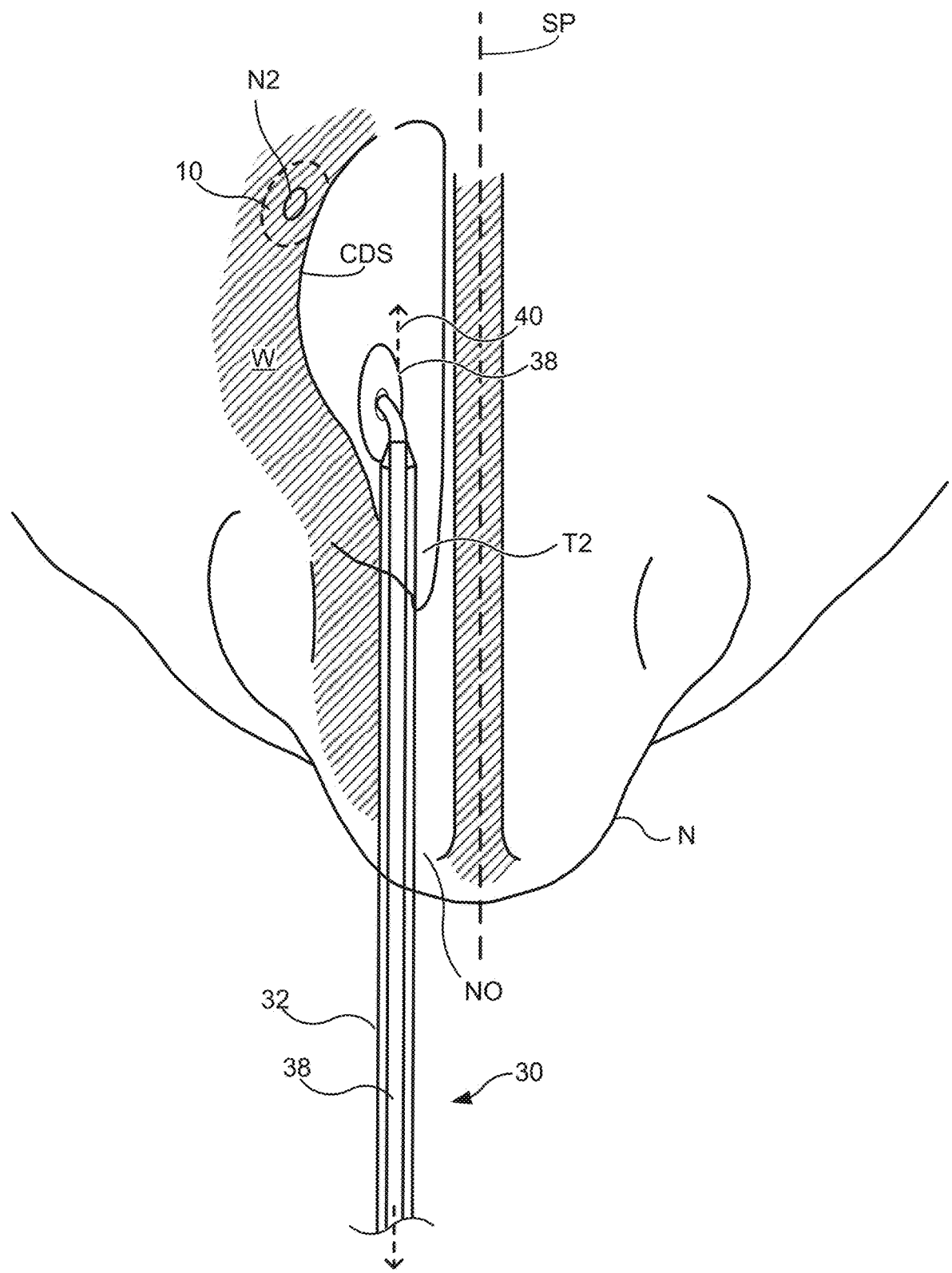
FIGS. 6A-6B illustrate the device of FIGS. 5A-5B in use within the nasal cavity.
Figure 6B:
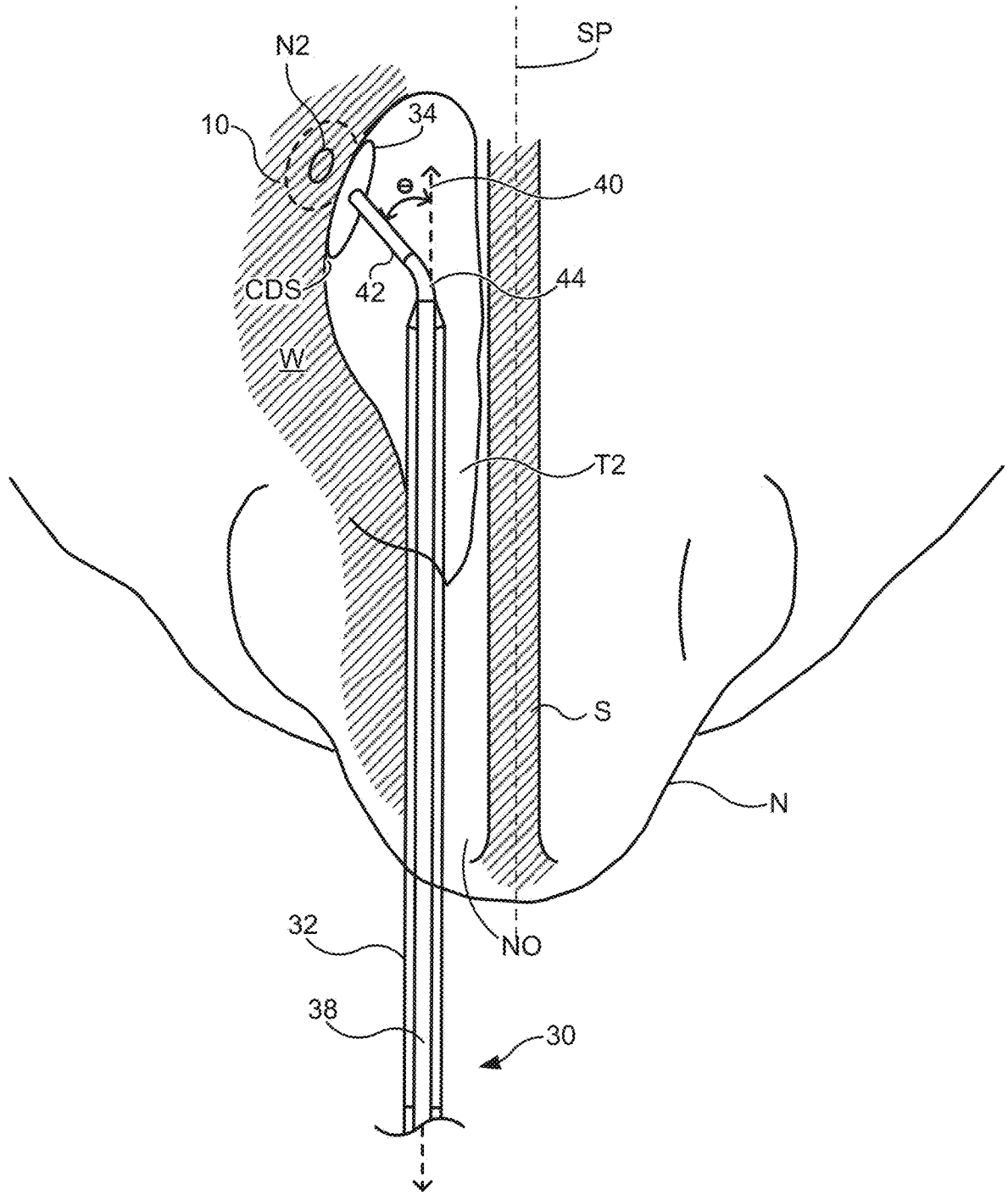

Probe 30 may be used in a therapeutic method wherein the target area may be treated without stretching the nostril or pressing against the septum. FIGS. 6A-6B illustrate the devices of FIGS. 5A-5B in use within the nasal cavity. During treatment, the probe 30 is placed in the first configuration with the end effector 34 proximate to the distal end of the outer shaft 32 and the distal end, i.e. end effector end, is inserted into the nostril of a patient. During this step, the end effector 34 may be in a deflated configuration. FIG. 6A illustrates the probe 30 after it has advanced partially into the nasal cavity. While the probe 30 is advanced it remains in the first confirmation as the end effector 34 travels from the nostril into the middle meatus. During this insertion, the longitudinal axis of the outer shaft 32 remains in a plane substantially parallel to the sagittal plane SP and is not angled to cause pressure against the septum and stretch the nostril. The probe 30 is continued to be advanced and is further inserted between and past the septum and the inner turbinate T3. The end effector 34 is advanced into the middle meatus by tucking the superior edge of the end effector 34 lateral to the middle turbinate and advancing probe 30 posteriorly and slightly superior along the inferior turbinate while keeping the end effector 34 underneath the middle turbinate T2. The probe 30 is advanced until the distal end of the end effector 34 touches the attachment of the middle turbinate T2 to the lateral wall within the cul-de-sac CDS. As shown in FIG. 6B, with the distal end of the outer shaft 32 tucked underneath the middle turbinate and the distal tip of the end effector touching attachment of the middle turbinate to the lateral wall, the inner shaft 38 is then advanced within the outer shaft 32 so that distal end portion 42 translates the end effector 34 laterally and posteriorly away from outer shaft 32 at a defined angle θ defined by angled tip 46 towards the target area 10. The inner shaft 38 may be advance until a distal end of the end effector 34 slides along the attachment and up against the target area 10 along the lateral wall W. With the distal end of the end effector 34 contacting the posterior aspect of the target area 10 the probe 30 may be further translated posteriorly or the end effector 34 may be further translated from the outer shaft 32 so that portions of the end effector 34 and/or the distal end portion 42 flex or rotate and cause the end effector 34 to increase the surface area of the end effector 34 contacting the target area 10 in a an anterior direction. Therefore, using probe 30 allows the end effector 34 to be positioned against the target area without substantially angling the probe shaft 32 and causing pressure against the septum or stretching of the nostril. Therefore this translation of force is more effective and more comfortable for the patient than angling a probe shaft, as shown in FIG. 4B. It may be appreciated, however, that in some instances the probe shaft 32 may additionally be angled to accommodate particular anatomical features. In such instances, such tilting will be substantially less than without the ability to laterally extend the end effector 34.

Once the end effector 34 is desirably placed against the target area 10, the therapy may be applied. Such therapy may include heat, such as thermoablation, or cold, such as cryotherapy (cryoablation). The cryogen liquid is delivered through a small delivery tube as described in commonly owned U.S. patent application Ser. No. 14/503,060 filed Sep. 30, 2014, entitled "APPARATUS AND METHODS FOR TREATING RHINITIS", which is incorporated herein by reference in its entirety for all purposes.

FIGS. 7A-7B an embodiment of a probe 50 that provides lateral support to the therapeutic end effector 54. In embodiments probe 50 allows the end effector 54 to be moved laterally while a portion of the probe shaft 52 maintains its position. Probe 50 comprises an elongate shaft 52 sized and configured to be advanceable through a nostril NO of a patient and along a nasal meatus, such as a middle meatus between an inferior and middle turbinate. The shaft 52 has a distal end 55 and a proximal end 57, wherein the end effector 54 is disposed at or along its distal end 55. In this embodiment, the end effector 54 comprises an inflatable sheath or balloon 56 mounted on the elongate shaft 52. In embodiments, the balloon 56 is configured for cryotherapy wherein the balloon 56 is fillable with a liquid cryogen that evaporates thus creating very low temperatures through the Joules-Thomson effect so as to deliver cold to a target area for cryoablation or cryomodulation thereto. In this embodiment, the probe 50 further includes a lateral support 58 which is disposed along the shaft 52 in a manner so as to provide support to the end effector 54 in a lateral direction when in use. In this embodiment, the lateral support 58 comprises an elongate rod, strip or ribbon extending along a side of the probe shaft 52, attached to the distal end 55 and then extending unattached toward the proximal end 57. A portion of the unattached support 58 extends through a lumen in the shaft 52 so as to be held flush with the shaft 52, parallel to a longitudinal axis 40 of the shaft 52. A remaining portion of the unattached support 58 remains free to move laterally away from the shaft 52, perpendicular to the longitudinal axis 40, so as to provide support in the lateral direction.

FIG. 7A illustrates the probe 50 in a collapsed configuration, wherein the balloon 56 is uninflated and the lateral support 58 is flush with the shaft 52 from the distal end 55 to the proximal end 57. The shaft 52 is easily insertable into a nostril NO in the collapsed configuration. FIG. 7A illustrates the shaft 52 oriented so that the balloon 56 faces the target area (not shown) and the lateral support 58, which is on the opposite side of the probe 50, faces a tissue surface T opposite the target area so that the lateral support 58 can be used for supporting the balloon 56. In the nose, the target area may, for example, reside along the lateral wall of the cul-de-sac and the opposite tissue surface would be the septum or other nearby tissue surfaces. FIG. 7B illustrates the probe 50 in an expanded configuration, wherein the balloon 56 is inflated for treatment and the lateral support 58 is extended so that a portion of the unattached portion bends, bows or flexes laterally outwardly from the longitudinal axis of the shaft 52 in the area of the end effector 54, as shown. Such expansion of the lateral support 58 is achieved by advancement of the lateral support 58 through the lumen in the shaft 52, toward the distal end 55. The lateral support 58 remains flush with the shaft 52 within the lumen during advancement but bows laterally outwardly from the shaft 52 upon exiting the lumen wherein the support 58 is free to move. In embodiments, the lateral support 58 is comprised of a flexible material such as Nitinol, Nylon, Spring steel, polyethylene, Teflon or polyurethane. The lateral support 58 is advanced so that it bows to a point where the distance between the further bowing of the lateral support and surface of the balloon causes the lateral support to contact the nearby tissue T and balloon to contact the target area, as shown. In some instances, the balloon 56 is sufficiently inflated to contact a target area while the shaft 52 remains aligned with the longitudinal axis 40. In such instances, the lateral support 58 may be bowed against the tissue T, opposite the target area, so as to hold the balloon 56 in position and apply lateral force to the balloon 56 and the target area. This applies pressure to the target area which may thin the tissue of the target area, bringing the balloon closer to the underlying target nerves. Such pressure may also reduce blood flow through the area. Both of these aspects may increase the penetration of the therapy, such as creating a deeper freeze zone.

In some instances, the inflated balloon 56 is not able to contact the target area while the shaft 52 remains aligned with the longitudinal axis 40. In such instances, the lateral support 58 may be further advanced through the lumen to allow for additional bowing against the tissue T, as illustrated in FIG. 7C. As more of the lateral support 58 is extended, increasing force is applied to the distal point of attachment of the lateral support 58 to the shaft 52 (here the lateral support 58 is attached at a distal tip 59 of the shaft 52). Such increasing force tips the distal end 55 of the shaft 52 away from the longitudinal axis 40, such as by an angle θ. In embodiments, the angle θ ranges from 10 degrees to 90 degrees, more particularly from 30 degrees to 60 degrees. This allows the balloon 56 to reach a more laterally positioned target area, such as within the cul-de-sac, while maintaining alignment of the proximal end 57 of the shaft 52 with the longitudinal axis 40.

Figure 8:
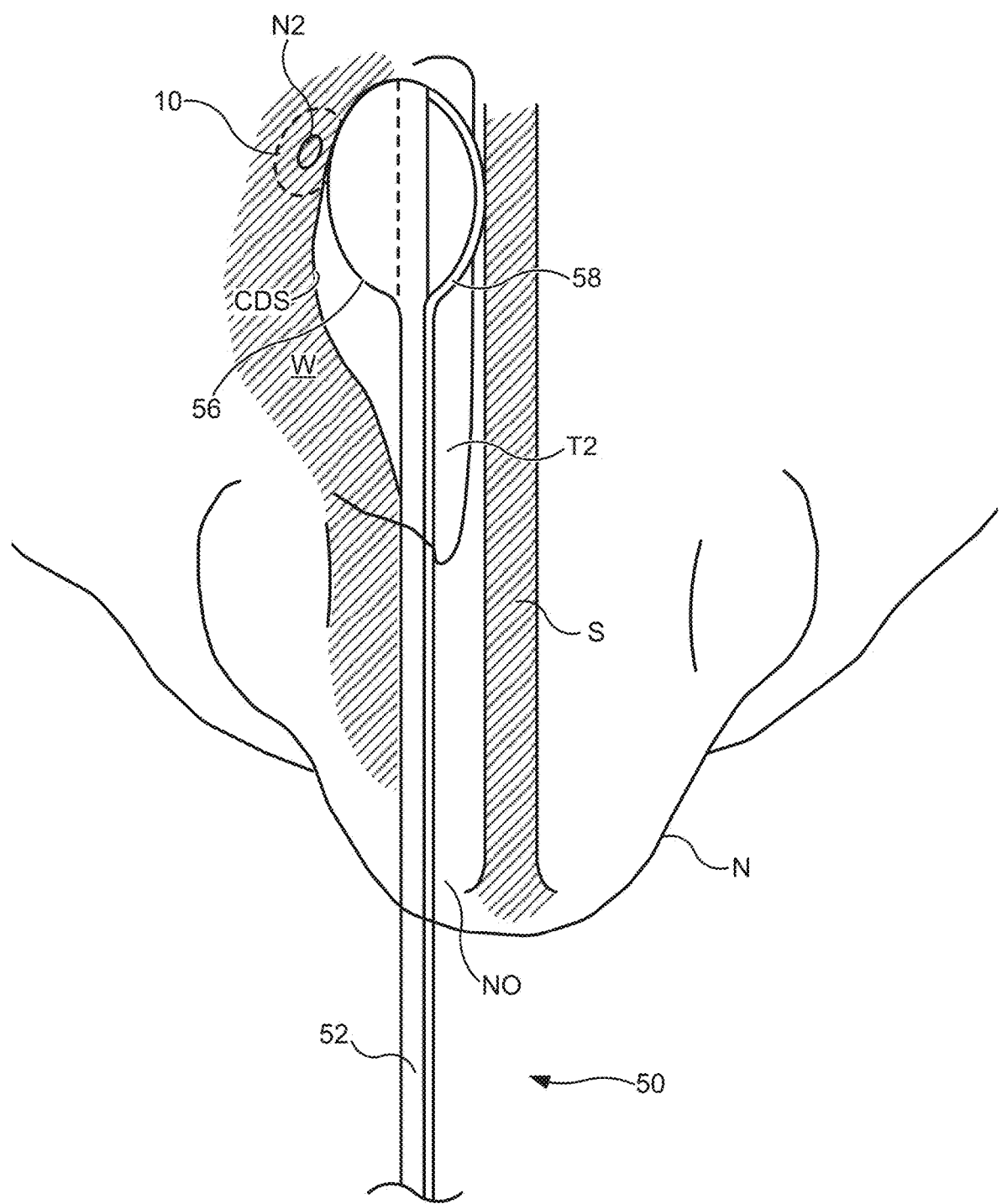
FIG. 8 illustrates the probe of FIGS. 7A-7C inserted into a nostril of a nose.

FIG. 8 illustrates the probe 50 of FIGS. 7A-7C inserted into a nostril NO of a nose N. The probe 50 may be advanced therein in the collapsed configuration of FIG. 7A. Once positioned so that the balloon 56 is desirably aligned with the target area 10 along the wall W of the cul-de-sac CDS, the balloon 56 is inflated and the lateral support 58 is advanced to allow lateral extension of the free moving portion of the lateral support 58. The lateral support 58 may laterally extend until it contacts the underside of the middle turbinate T2 and/or the septum S and provides pushback and lateral support to the inflated balloon 56. In some instances, the support 58 is further extended to push the balloon 56 against the target area 10. This assists in applying pressure to the target area 10, potentially reducing the distance between the balloon 56 and the underlying target nerve N2. The support 58 also assists in maintaining such contact and pressure against the target area 10 during the therapeutic procedure, such as cryotherapy. This support may improve the treatment outcome by providing consistent and thorough contact, reducing the distance between the applied therapy and the target nerve N2, reducing blood flow and reducing patient discomfort related to probe movement and tilting.

In embodiments, the lateral support 58 may be attached to the shaft 52 at any suitable location, such as at any distance from the distal tip 59. Variation in the location of the attachment point may create lateral support at different locations along the shaft 52. Such variation may provide different locations of pressure application by the balloon 56. Such variation may also provide different angles of tipping of the distal end of the shaft 52. In embodiments, the support 58 may be held to the shaft 52 by features other than passing through a lumen in the shaft 58. For example, the support 58 may be mounted on the exterior of the probe shaft 52, passing beneath various straps or through various eyelets which hold the support 58 near or against the shaft 52. Likewise, the support 58 may be slidably attached to the shaft 52 at one or more points in addition to the attachment point. Such slidable attachment points may be achieved by passing the support 58 through a short lumen in the shaft 52 or beneath a strap or through an eyelet exterior to the shaft 52. Thus, as the support 58 is advanced, the support 58 is able to bow or bend laterally outwardly around the attachment points, creating more than one lateral support.

Figure 9:
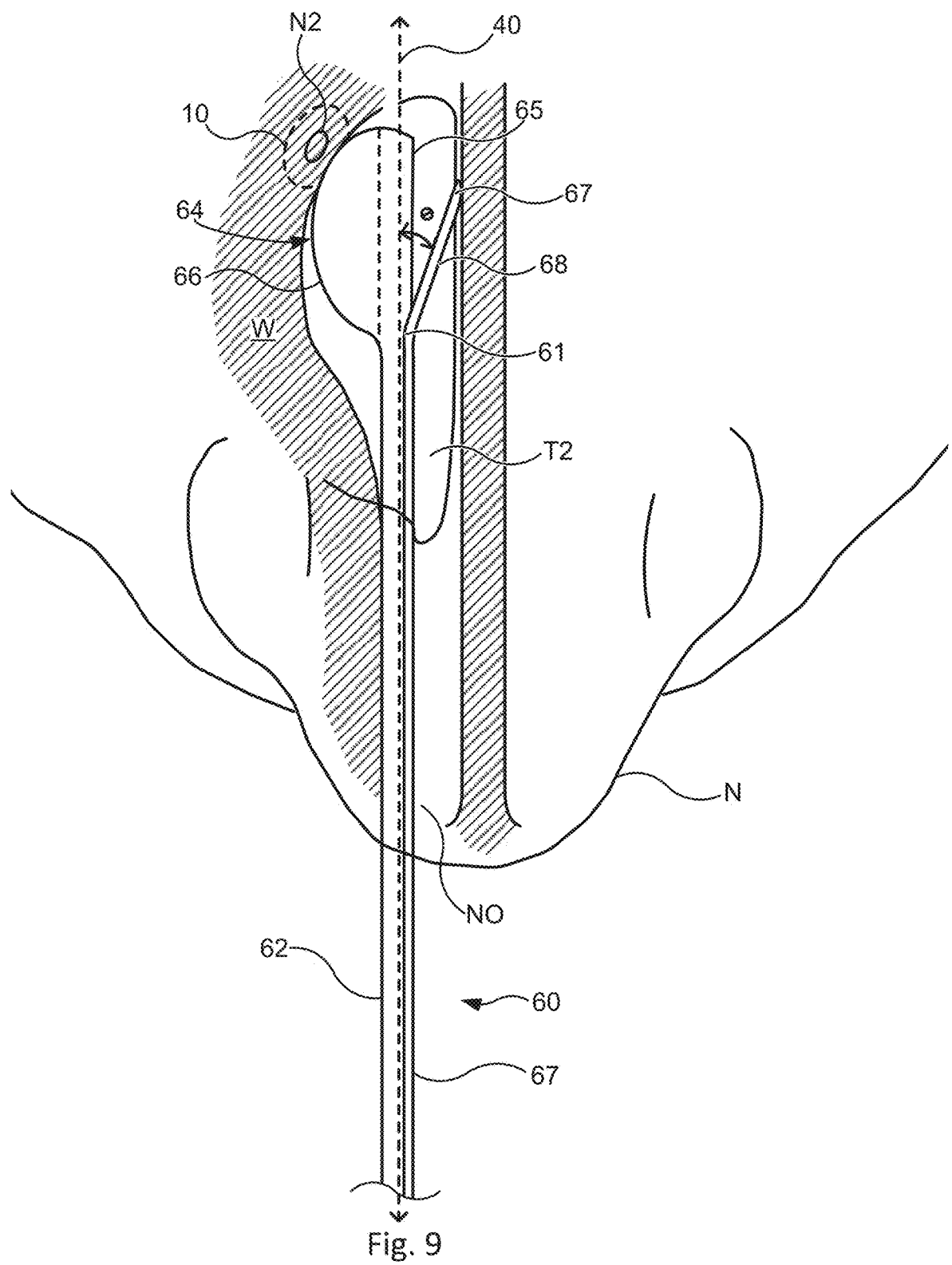
FIG. 9 illustrates an embodiment of a probe having a free end that provides lateral support to the therapeutic end effector.

FIG. 9 illustrates another embodiment of a probe 60 that provides lateral support to the therapeutic end effector 64, and in some instances allows the end effector 64 to be moved laterally while a portion of the probe shaft 62 maintains its position. In this embodiment, the probe 60 comprises an elongate probe shaft 62 sized and configured to be advanceable through a nostril NO of a patient and along a nasal meatus, such as a middle meatus between an inferior and middle turbinate. The shaft 62 has a distal end 65 and a proximal end 67, wherein the end effector 64 is disposed at or along its distal end 65. In this embodiment, the end effector 64 comprises an inflatable sheath or balloon 66 mounted on the elongate shaft 62. In embodiments, the balloon 66 is configured for cryotherapy wherein the balloon 66 is fillable with a cryogenic liquid so as to deliver cold to a target area for cryoablation or cryomodulation thereto. In this embodiment, the probe 60 further includes a lateral support 68 which is disposed along the shaft 62 in a manner so as to provide support to the end effector 64 in a lateral direction when in use. In this embodiment, the lateral support 68 comprises an elongate rod, strip or ribbon extending within a lumen along a side of the probe shaft 62, parallel to a longitudinal axis 40. The lateral support 68 is not attached to the shaft 62 or the balloon 66. The support 68 is advanceable through the lumen and has a hinge, kink point or pre-formed bend 61 near the distal end of the lateral support configured so that when the bend 61 is advanced out of the lumen, a distal tip 67 of the support 68 is moves laterally outward, away from the shaft 62 and balloon 66. In embodiments, the lateral support 68 is comprised of nitinol or a shape-memory material, and the lateral support 68 may revert to its pre-formed shape, moving the distal tip 67 outward, perpendicular to the longitudinal axis 40, so as to provide support in the lateral direction. In embodiments, the distal end of the support 68 forms an angle $\theta$ with the longitudinal axis. In some embodiments, the angle $\theta$ ranges from 10 degrees to 90 degrees, more particularly from 30 degrees to 60 degrees.

In embodiments, the inflated balloon 66 is not able to contact the target area while the shaft 62 remains aligned with the longitudinal axis 40. In embodiments, a lateral support 68 may be used having a bend 61 located at a further distance from the distal tip 67. This causes more of the support 68 to be extended laterally outwardly. Likewise, the support 68 may be positioned so that the bend 61 is disposed near the distal tip 69 of the shaft 62. Thus, as more of the support 68 is extended the force applied to the distal tip 69 of the shaft 62 is increased. Such increasing force tips the distal end 65 of the shaft 62 away from the longitudinal axis 40. This allows the balloon 66 to reach a more laterally positioned target area, such as within the cul-de-sac, while maintaining alignment of the proximal end 67 of the shaft 62 with the longitudinal axis 40.

Referring again to FIG. 9, in embodiments, the probe 60 is advanceable into the nostril NO of the nose N in a collapsed configuration, wherein the support 68 is against the shaft 62 and the balloon 66 is not inflated. Once positioned so that the balloon 66 is desirably aligned with the target area 10 along the wall W of the cul-de-sac CDS, the balloon 66 is inflated and the support 68 is advanced at least until the bend 61 is allowed to laterally extend the free end of the support 68. The free end of the support 68 laterally extends until its distal tip 67 contacts the underside of the middle turbinate T2 and/or the septum S and is able to provide pushback and lateral support to the inflated balloon 66. In some instances, the support 68 is further extended to push the balloon 66 against the target area 10. This assists in applying pressure to the target area 10, potentially reducing the distance between the balloon 66 and the underlying target nerve N2. The support 68 also assists in maintaining such contact and pressure against the target area 10 during the therapeutic procedure, such as cryotherapy. This support may improve the treatment outcome by providing consistent and thorough contact, reducing the distance between the applied therapy and the target nerve N2, reducing blood flow and reducing patient discomfort related to probe movement and tilting.

In embodiments, the bend 61 may be disposed at any suitable location, such as at any distance from the distal tip 67. Likewise, the support 68 may be advanced or retracted to position the bend 61 at any location along the probe shaft 62. Variation in the location of the attachment point may create lateral support at different locations along the shaft 62. Such variation may provide different locations of pressure application by the balloon 66. Such variation may also provide different angles of tipping of the distal end of the shaft 62. In embodiments, the support 68 may be held to the shaft 62 by features other than passing through a lumen in the shaft 62. For example, the support 68 may be mounted on the exterior of the probe shaft 62, passing beneath various straps or through various eyelets which hold the support 68 near or against the shaft 62.

FIGS. 10A-10B, 11A-11B illustrate embodiments of probes 70 having end effectors 74 that extend in a lateral direction to reach target areas along the cul-de-sac while a portion of the probe shaft 72 maintains its position. In embodiments, the probe 70 comprises an elongate probe shaft 72 sized and configured to be advanceable through a nostril NO of a patient and along a nasal meatus, such as a middle meatus between an inferior and middle turbinate. The shaft 72 has a distal end 75 and a proximal end (not shown), wherein the end effector 74 is disposed at or along its distal end 75. The end effector 74 comprises an inflatable or non-inflatable sheath or balloon 76 having an internal expander 78. The balloon 76 may be configured for cryotherapy wherein the balloon 76 is fillable with a cryogenic liquid so as to deliver cold to a target area for cryoablation or cryomodulation thereto. The internal expander 78 acts as a scaffolding and is comprised of a suitable material for providing such structure, such as metal or polymer wire, filament, nitinol, or the like. The material is flexible so as to be atraumatic yet rigid so as to provide support to the balloon 76, particularly when used uninflated. The expander 78 comprises a longitudinal segment 79 which is aligned with a longitudinal axis 40 of the elongate probe shaft 72. The longitudinal segment 79 is connected with a pullwire 82, or is continuous to act as a pullwire 82, extending through the probe shaft 72, typically to its proximal end. The expander 78 also includes at least one expanding segment 80. FIG. 10A illustrates an embodiment having two expanding segments 80, one on each side of the longitudinal segment 79. The expanding segments 80 are fixedly attached to the longitudinal segment 79 at a first location 84, such as at or near its distal tip, and slidably attached at a second location 86 proximal to the first location 84. In this embodiment, each expanding segment 80 has a hinge, kink point, or flex point 88. Retraction of the pullwire 82, retracts the longitudinal segment 79. As the first location 84 is drawn toward the probe shaft 72, the second location 86 is restricted from being drawing into the probe shaft 72, therefore causing each expanding segment 80 to move laterally outward at its flex point 88, as illustrated in FIG. 10B. Thus, the flex points 88 move in direction perpendicular to the longitudinal axis 40. The expander 78 is now in an expanded position, structurally supporting the balloon 76. In embodiments, the flex points 88 may be located at a variety of positions to vary the shape of the expander 78 in the expanded position. Likewise, each expanding segment 80 may include more than one flex point 88.

FIGS. 11A-11B illustrate a similar embodiment of an expander 78. FIG. 11A illustrates an embodiment having four expanding segments 80, two on each side of the longitudinal segment 79. The expanding segments 80 are fixedly attached to the longitudinal segment 79 at a first location 84, such as at or near its distal tip, and slidably attached at a second location 86 proximal to the first location 84. Here, each expanding segment 80 is sufficiently flexible so as to bow without a flex point. Retraction of the pullwire 82, retracts the longitudinal segment 79. As the first location 84 is drawn toward the probe shaft 72, the second location 86 is restricted from being drawing into the probe shaft 72, therefore causing each expanding segment 80 to bow laterally outward, as illustrated in FIG. 11B. Thus, the expanding segments 80 move in a direction perpendicular to the longitudinal axis 40. The expander 78 is now in an expanded position, structurally supporting the balloon 76.

Figure 12A:
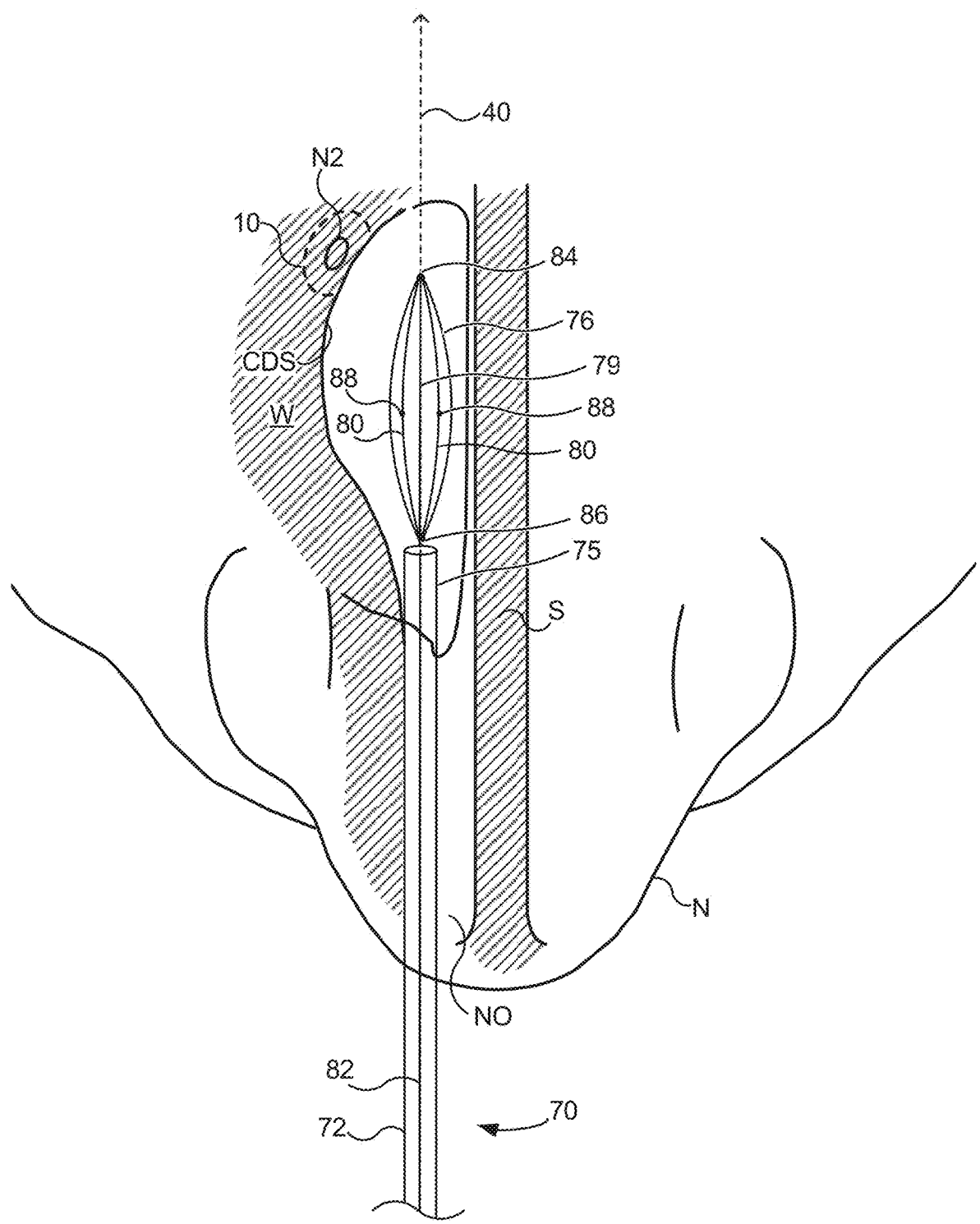
FIGS. 12A-12B illustrate an example of the end effector embodiment of FIGS. 10A-10B in use.
Figure 12B:
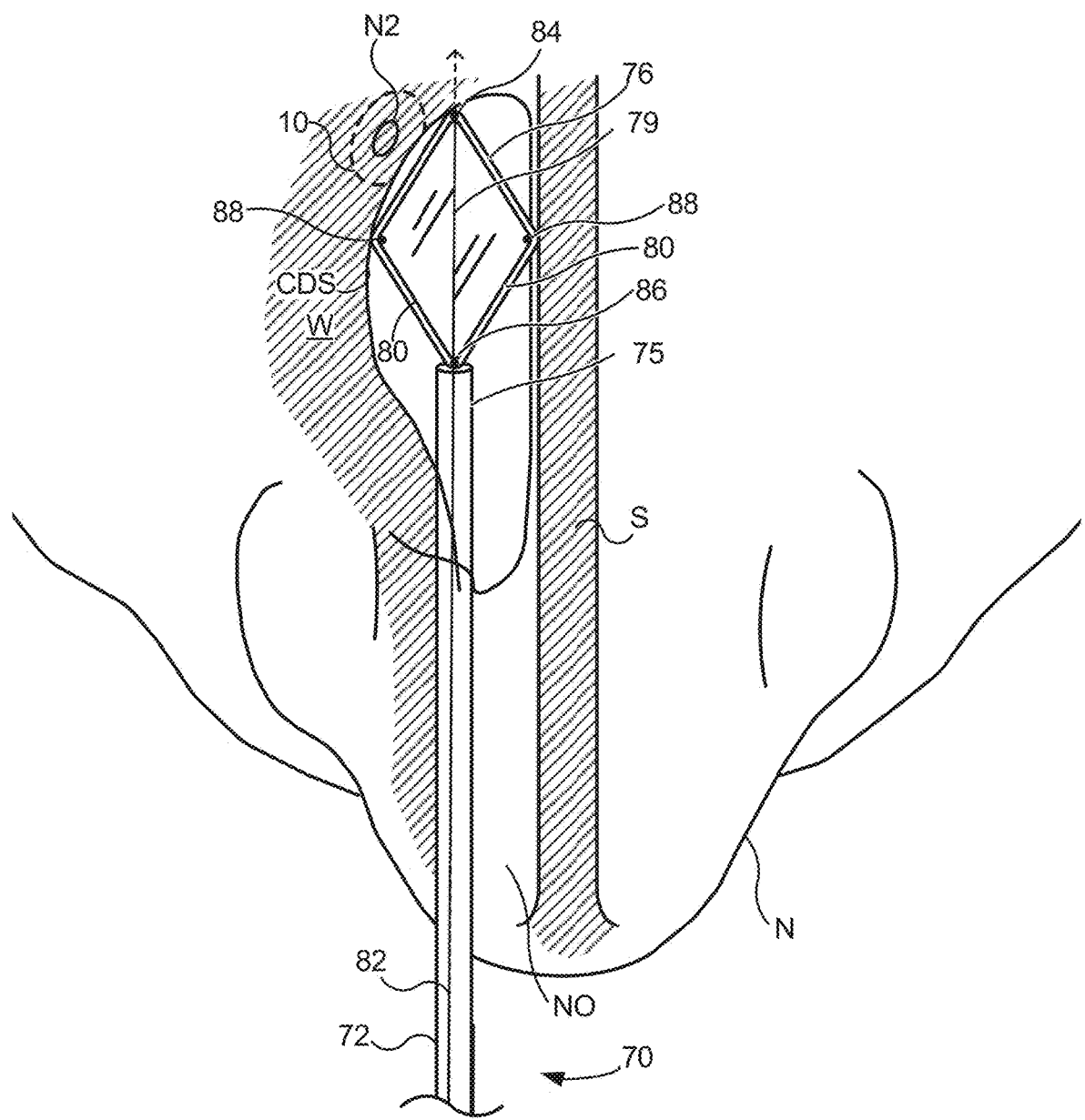

FIGS. 12A-12B illustrate the end effector 74 embodiment of FIGS. 10A-10B in use. FIG. 12A illustrates the probe 70 is inserted into the nostril NO of the nose N in a collapsed configuration, wherein the expanding segments 80 are substantially aligned with the longitudinal axis 40. Once positioned so that the balloon 76 is desirably aligned with the target area 10 along the wall W of the cul-de-sac CDS, the 78 is expanded as illustrated in FIG. 12B. Here, the pullwire 82 is retracted, retracting the longitudinal segment 79. As the first location 84 is drawn toward the probe shaft 72, the second location 86 is restricted from being drawn into the probe shaft 72, therefore causing each expanding segment 80 to move laterally outward at its flex point 88. The probe 70 is positioned so that at least one flex point 88 contacts the nasal wall W while the probe shaft 72 maintains its position in the nostril NO. FIG. 12B illustrates the at least one flex point 88 contacting the target area 10 so as to apply pressure thereto, improving therapy to the underlying nerve N2. FIG. 12B also illustrates at least one flex point 88 contacting the septum S to provide a backstop or lateral support to the end effector 74. This may also be used to increase pressure applied to the target area. In embodiments, the expander may have only one expanding segment 80 if desired, such as to contact the lateral nasal wall W. In such instances, firmly holding the probe may be sufficient back support. In embodiments, the expander 78 may be used in combination with a mechanism for delivery of cryogen to the balloon 76, or the expander 78 itself may serve as a cryoline.

FIGS. 13, 14A-14B, 15, 16 illustrate an embodiment of a probe 100 that provides lateral support to the therapeutic end effector 104. In this embodiment, the probe 100 comprises an elongate probe shaft 102 sized and configured to be advanceable through a nostril NO of a patient and along a nasal meatus, such as a middle meatus between an inferior and middle turbinate. The shaft 102 has a distal end 105 and a proximal end (not shown), wherein the end effector 104 is disposed at or along its distal end 105. In this embodiment, the end effector 104 comprises a non-inflatable sheath or balloon 106 mounted on the elongate shaft 102. In this embodiment, the end effector 104 is configured for cryotherapy and includes a cryoline 103 for delivery of cryogen to deliver cold to a target area for cryoablation or cryomodulation thereto. In this embodiment, the probe 100 further includes a lateral support 108 which is disposed along the shaft 102 in a manner so as to provide support to the balloon 106 in a lateral direction when in use. In this embodiment, the lateral support 108 comprises an elongate rod 110 extending along a side of the probe shaft 102, parallel to a longitudinal axis 40, such as within a lumen or within attachment features. The elongate rod 110 has a curved distal end 112. In this embodiment, the distal end 112 has a curvature of approximately 90 degrees so that the distal end 112 is substantially perpendicular to the longitudinal axis 40. However, other curvatures may be used, such as 45-135 degrees. In embodiments, the elongate rod 110 is malleable so that the curvature may be adjusted as needed.

In this embodiment, the elongate rod 110 is rotatable, advanceable and retractable. FIGS. 14A-14B illustrates an end view of the end effector 104 of FIG. 13 while the elongate rod 110 is in various positions. FIG. 14A illustrates the elongate rod 110 positioned so that the distal end 112 is parallel with the broad surface of the balloon 106. The elongate rod 110 is typically in this position during insertion into the nostril NO so as to minimize dimension. Once the balloon 106 is desirably placed near the target area, the elongate rod 110 is rotated, as illustrated in FIG. 14B, so that the distal end 112 is substantially perpendicular to the broad surface of the balloon 106. This allows the elongate rod 110 to apply force to the balloon 106, as will be illustrated later. FIG. 15 provides a side view illustration of the end effector 104 of FIG. 14B. As shown, the distal end 112 of the elongate rod 110 extends laterally outwardly, away from the longitudinal axis 40.

FIG. 16 illustrates the probe 100 of FIG. 13 in use, treating a target area 10 along the cul-de-sac CDS of the nasal cavity. In embodiments, the probe 100 is inserted into the nostril NO of the nose N in a collapsed configuration, wherein the elongate rod 110 is rotated so that its distal end 112 is disposed along a broad surface of the balloon 106. Once positioned so that the balloon 106 is desirably aligned with the target area 10 along the wall W of the cul-de-sac CDS, the rod 110 is rotated so that the distal end 112 is moved laterally away from the balloon 106. The distal end 112 is positioned against the middle turbinate T2 and/or septum S to provide a backstop or lateral support to the balloon 106. In some embodiments this stabilizes the balloon 106 and in other embodiments this also applies pressure to the target area 10, improving therapy to the underlying nerve N2. In embodiments, the distal end 112 may be positioned against any suitable tissue so as to provide desired support. Likewise, the elongate rod 110 may be rotated by any amount so that the distal end 112 is perpendicular to the broad surface of the balloon 106 or positioned at any angle in relation to the balloon. Further, the rod 110 may be advanced or retracted in relation to the probe shaft 102 so as to position the distal end 112 at various locations along the balloon 106. In embodiments, the probe shaft 102 may tilt slightly within the nostril NO to allow the end effector 104 to sufficiently contact the target area 10. However, such tilting is greatly diminished in comparison to such treatment without the lateral support 108.

Figure 17A:
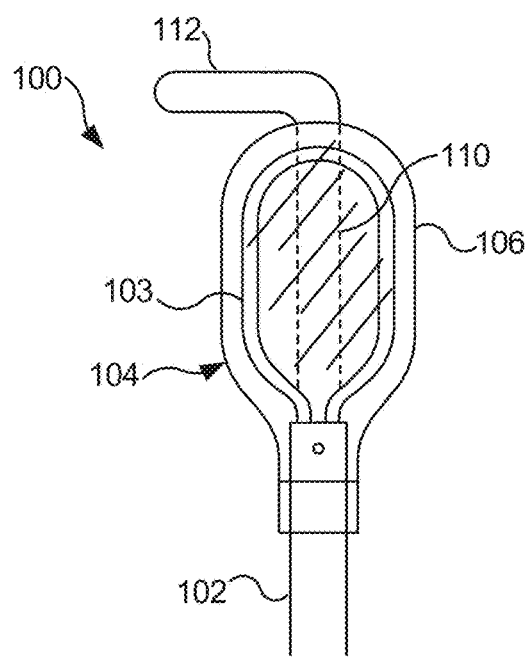
FIGS. 17A-17D illustrate an embodiment of a probe wherein a lateral support is advanceable so that its distal end is positionable distally, beyond an end effector.
Figure 17B:
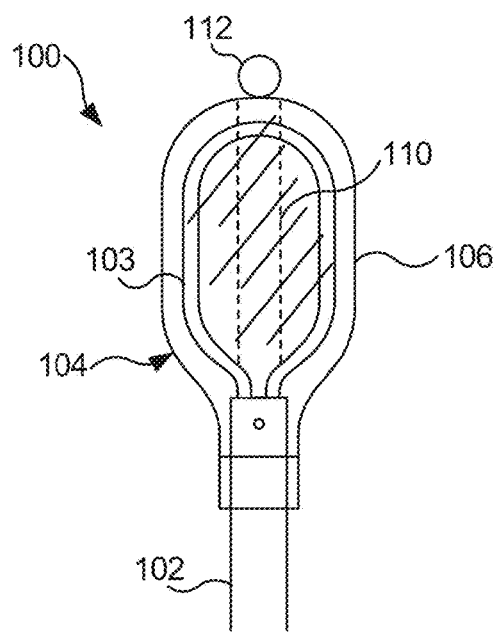
Figure 17C:
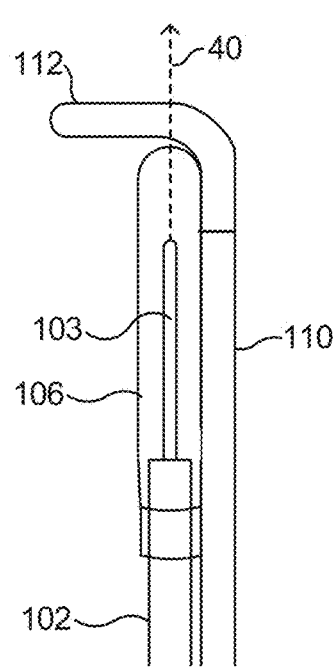
Figure 17D:
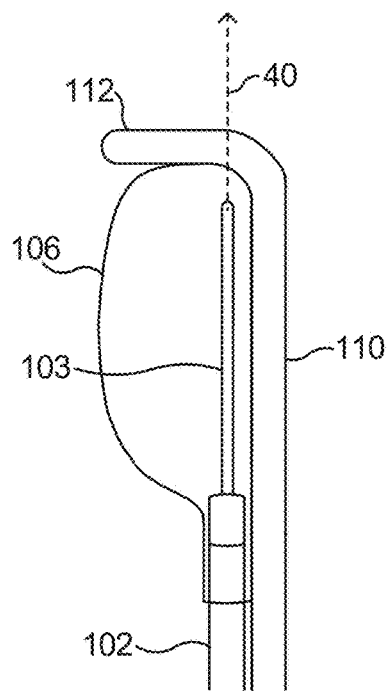

In some embodiments, the elongate rod 110 is advanceable so that the distal end 112 is positionable distally, beyond the balloon 104, as illustrated in FIGS. 17A-17D. Again, the elongate rod 110 is rotatable so that the distal end 112 can be positioned parallel with the broad surface of the balloon 106, as illustrated in FIG. 17A. The elongate rod 110 is typically in this position during insertion into the nostril NO so as to minimize dimension. Once the balloon 106 is desirably placed near the target area, the elongate rod 110 is rotated, as illustrated in FIG. 17B, so that the distal end 112 extends over the balloon 106, substantially perpendicular to the broad surface of the balloon 106 (facing out of the page). This allows the elongate rod 110 to apply back support to the balloon 106, as will be illustrated later. FIG. 17C provides a side view illustration of the end effector 104 of FIG. 17B. As shown, the distal end 112 of the elongate rod 110 extends over the balloon 106, laterally outwardly, away from the longitudinal axis 40. In this embodiment, the balloon 106 is inflatable. FIG. 17D illustrates the balloon 106 in the inflated state. As shown, the balloon 106 favors expansion away from the rod 110, the rod 110 providing back support and stability for the balloon 106.

Figure 18A:
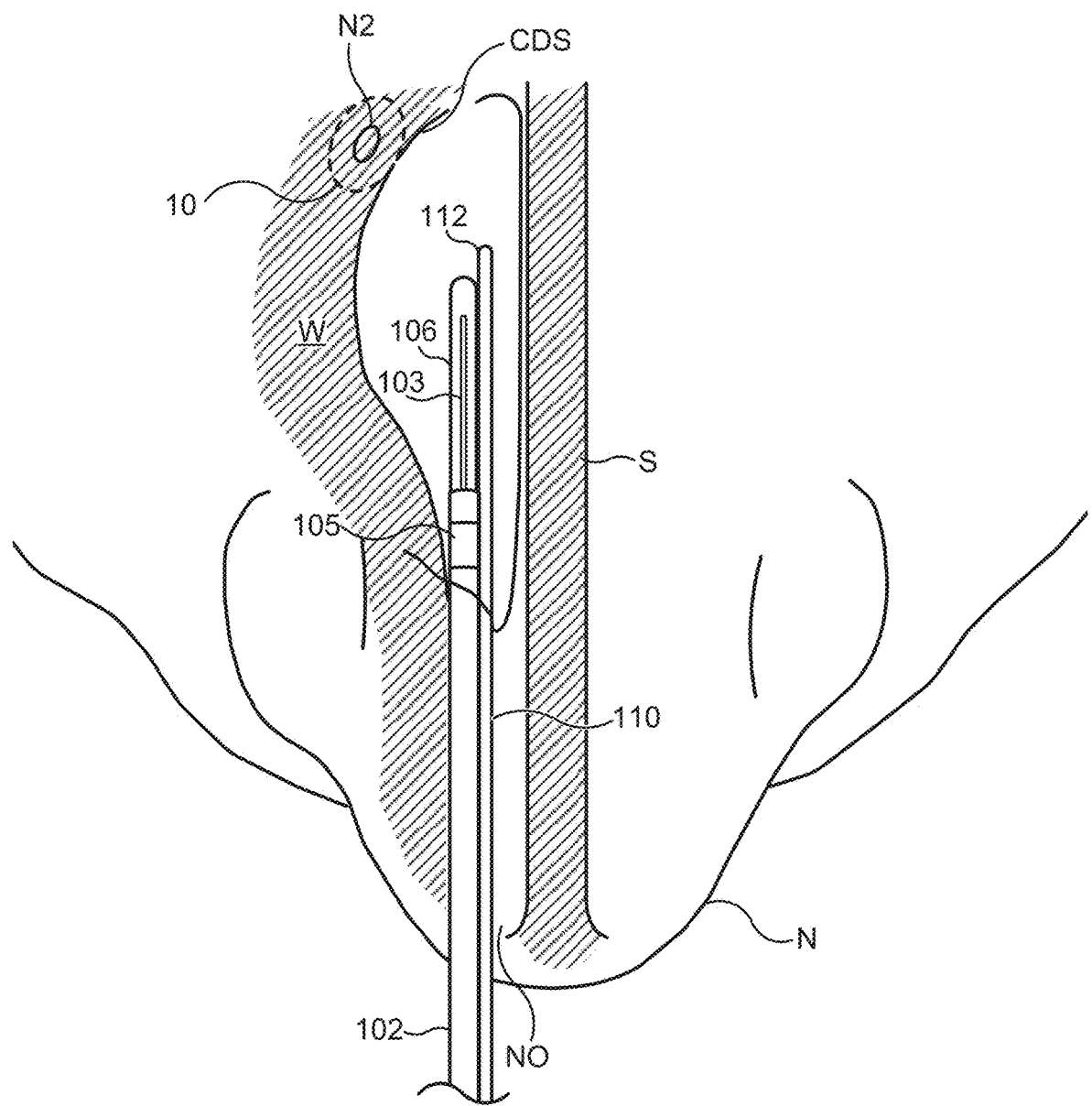
FIGS. 18A-18B illustrates an example of the embodiment of FIGS. 17A-17D in use.
Figure 18B:
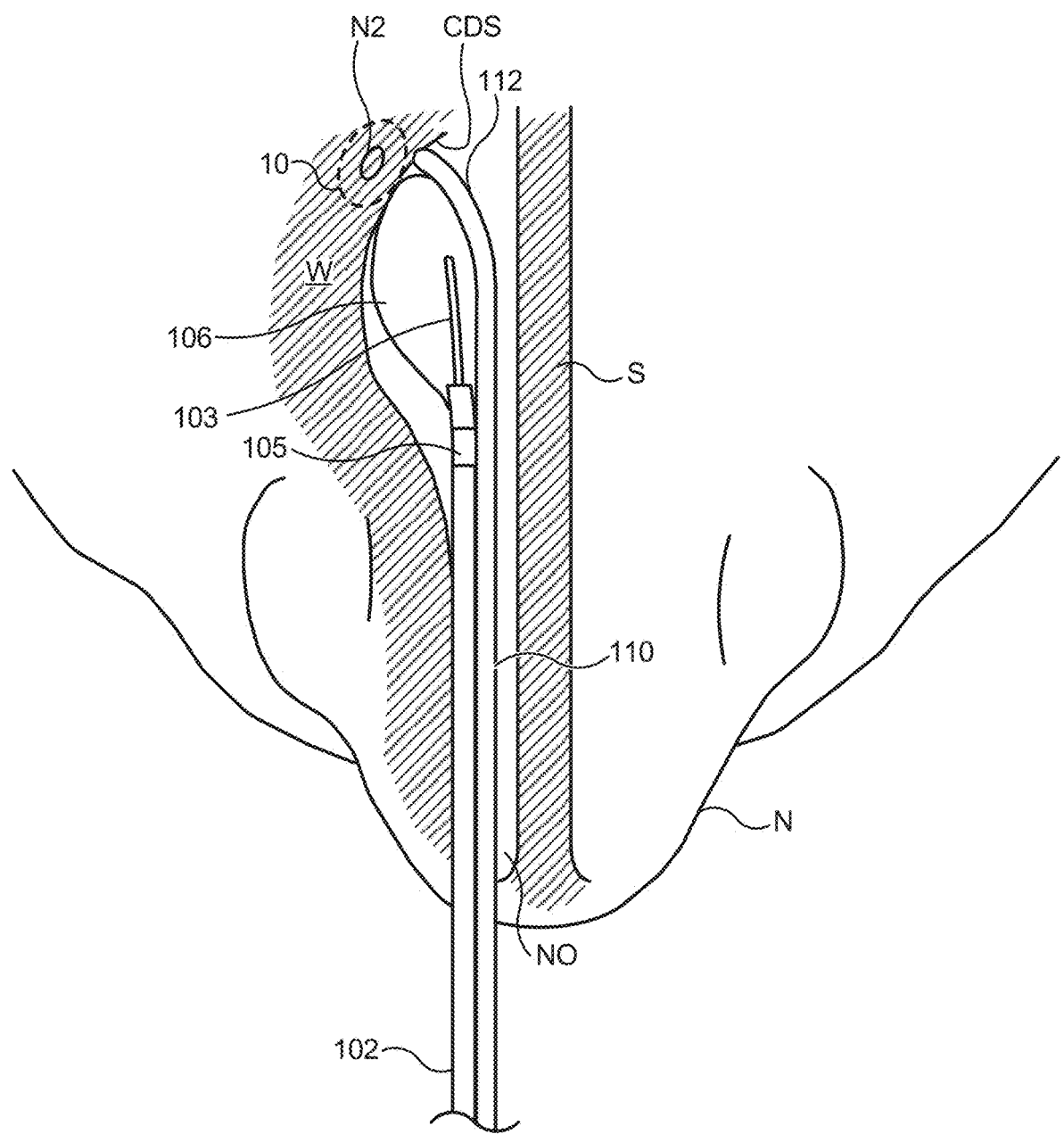

FIGS. 18A-18B illustrates the embodiment of FIGS. 17A-17D in use, treating a target area 10 along the cul-de-sac CDS of the nasal cavity. In embodiments, the probe 100 is inserted into the nostril NO of the nose N in a collapsed configuration, wherein the elongate rod 110 is rotated so that its distal end 112 is disposed along a broad surface of the balloon 106, as illustrated in FIG. 18A. Here, the curvature of the rod 110 is not visible as the distal end 112 is extending into the page. Once positioned so that the balloon 106 is desirably aligned with the target area 10 along the wall W of the cul-de-sac CDS, the rod 110 is rotated so that the distal end 112 is moved laterally toward the balloon 106, extending over the distal most end of the balloon 106. The distal end 112 is positioned against the lateral nasal wall W, near the target area 10, as illustrated in FIG. 18B. In embodiments, the distal end 112 may be malleable so as to adjust the curvature to accommodate various anatomies. The balloon 106 is inflated prior to, after or during positioning of the distal end 112 against the lateral wall W. The rod 110 directs the balloon 106 toward the wall W and provides back support to stabilize the position of the balloon 106 and increase contact with the wall W. In some embodiments, the rod 110 also assists in applying pressure to the target area 10, improving therapy to the underlying nerve N2. Typically, the rod 110 and probe shaft 12 maintains position with the nostril NO during the procedure, however it may be appreciated that the probe shaft 102 may tilt slightly within the nostril NO to allow the end effector 104 to sufficiently contact the target area 10. However, such tilting is greatly diminished in comparison to such treatment without the lateral support 108. Likewise, it may be appreciated that the rod 110 may tilt while the probe shaft 102 remains in position so as to increase pressure on the balloon 106 and/or wall W.

Figure 19A:
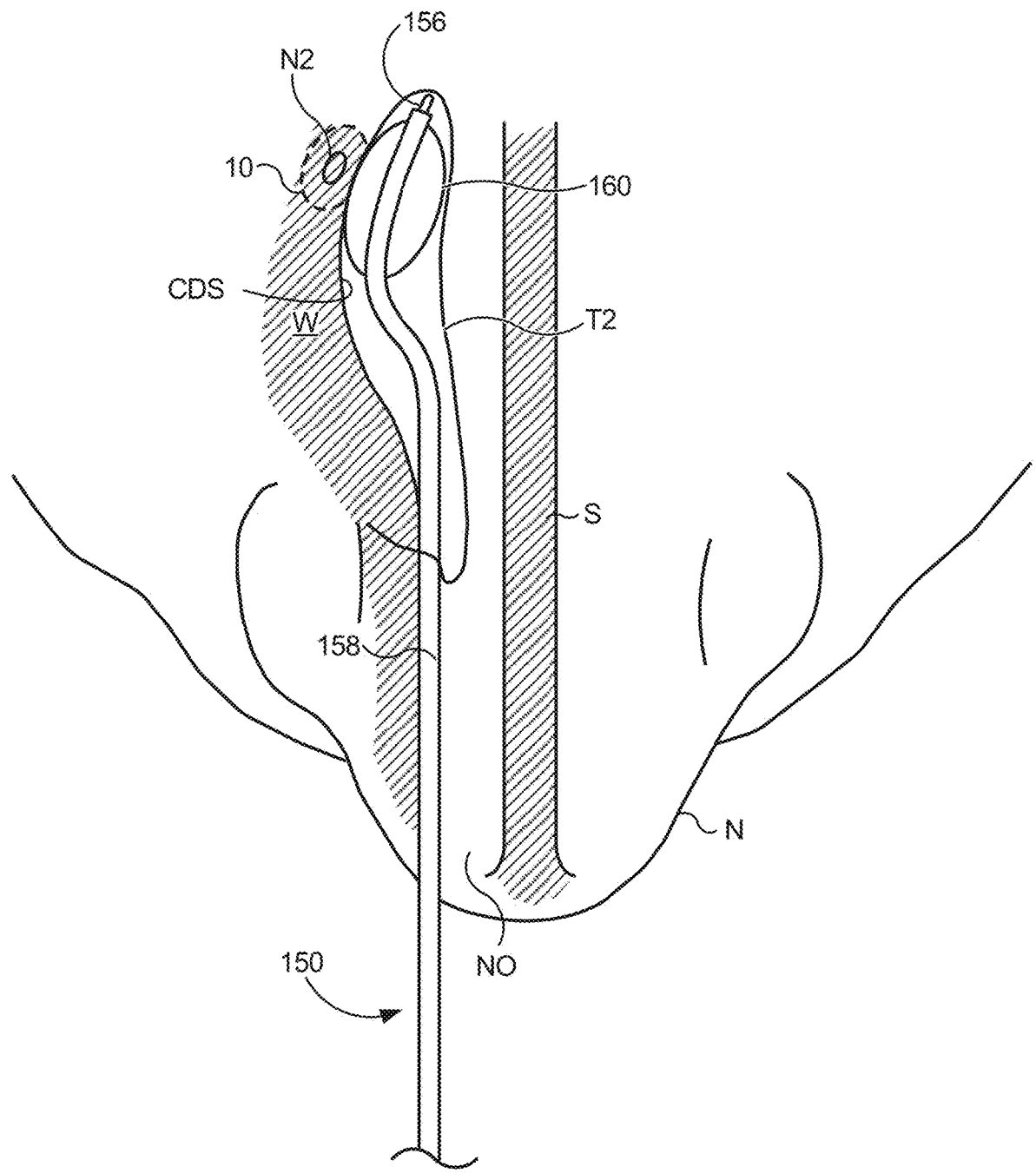
FIG. 19A illustrates an embodiment of a system that assists in guiding and maintaining a therapeutic end effector in a lateral direction to reach a target area along the cul-de-sac of the nasal cavity.

FIG. 19A illustrates an embodiment of a system 150 that assists in guiding and maintaining a therapeutic end effector 154 in a lateral direction to reach a target area 10 along the cul-de-sac CDS of the nasal cavity. In this embodiment, the system 150 comprises a curved stylet or guidewire 156 and a catheter 158 advanceable over the guidewire 156. The catheter 158 includes an inflatable sheath or balloon 160, typically configured for cryotherapy wherein the balloon 160 is fillable with cryogen so as to deliver cold to the target area 10 for cryoablation or cryomodulation thereto. In this embodiment, the guidewire 156 is advanceable through a nostril NO of a patient and along a nasal meatus, such as a middle meatus between an inferior and middle turbinate. The guidewire 156 may be pre-curved or malleable to allow the curvature to be determined during the procedure. The curvature may take a variety of forms, but generally causes the catheter 158 passed there over to bend toward the lateral wall W, such as to follow the curvature of the cul-de-sac CDS. This allows the balloon 160 to be positionable against the lateral wall W, more particularly against the target area 10 so as to treat the underlying nerve N2. In addition, the curvature maintains placement of the balloon 160 in the desired position and reduces any tendency for the balloon 160 to slip out of position during inflation and/or subsequent therapy.

Figure 19B:
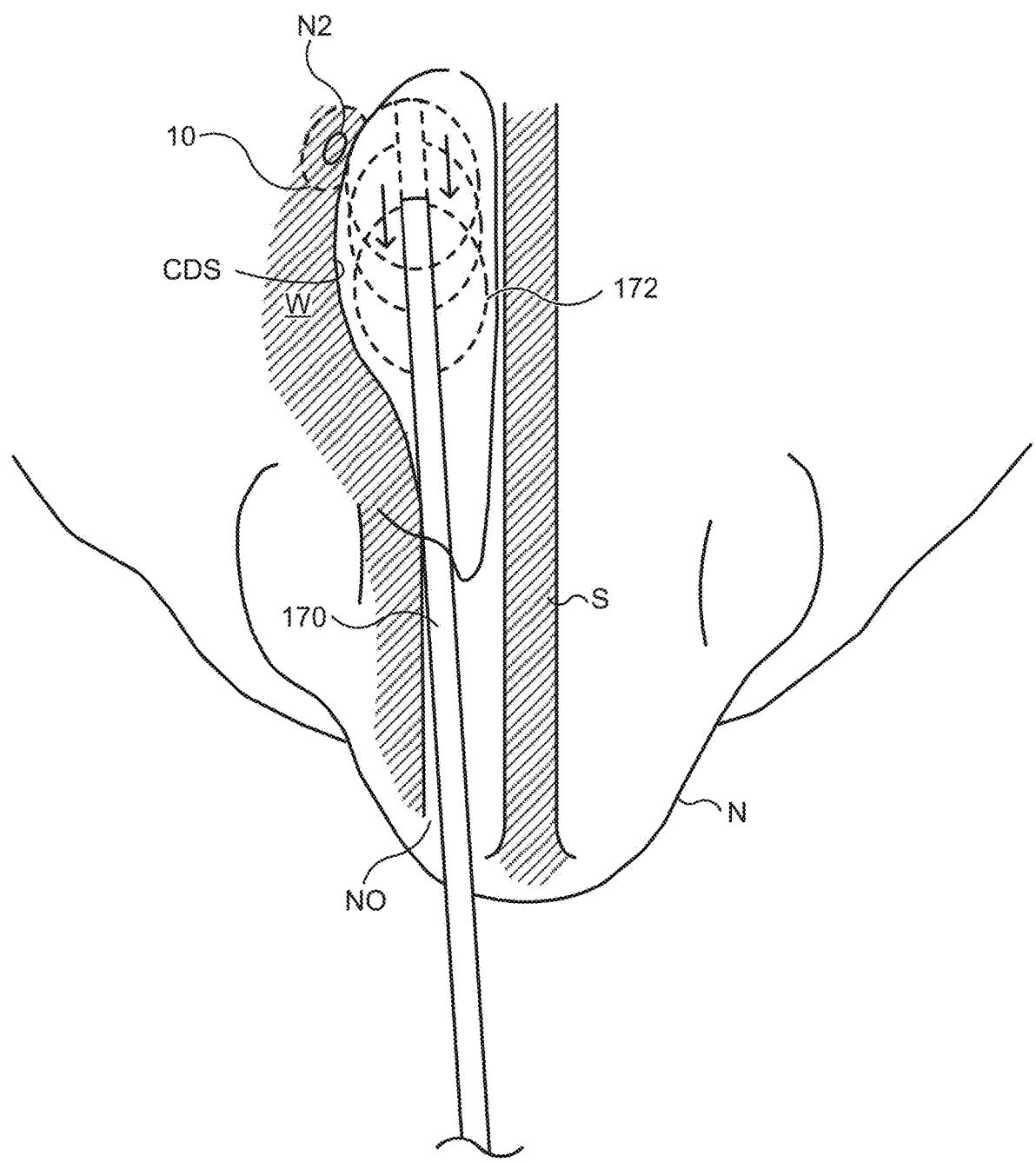
FIG. 19B illustrates a similar catheter in use without a curved guidewire.

FIG. 19B illustrates a probe 170 similar to probe 20 with the end effector comprising of a balloon 172. Probe 170 is positioned similar to probe 20 above where it is tilted laterally over the inferior turbinate T3 and underneath the middle turbinate T2 and into the cul-de-sac CDS, so that the distal end of the balloon 172 makes contact with the posterior aspect of the target area 10. Once the distal portion of the probe is positioned in the cul-de-sac contacting the target area 10 and lateral side of the middle turbinate T2, the balloon 172 is expanded pressing the remainder of the balloon surface area against the target area 10 as the other side of the balloon presses against the lateral side of the middle turbinate T2. The expansion occurs by the pressure build of the exhaust gas of the cryogen. This pressure can be as high as 750 psi, but will be tailored to 10-60 psi. Expansion of balloon 172 ranges from 0.5-20 mm, more probably 0.7-10 mm. The balloon 172 can be made of non-compliant, compliant, or semi-compliant thin walled materials. In embodiments, a semi-compliant thin walled material such as Nylon or a blend of Nylon is used. The wall thickness may be less than 0.005", and further may be less than 0.002". The expansion is generated using the cryogen exhaust therefore at the initiation of the cryogen the balloon material sticks preventing the balloon from dislodging or moving from the target area once therapy has begun.

Figures 20A, 20B:
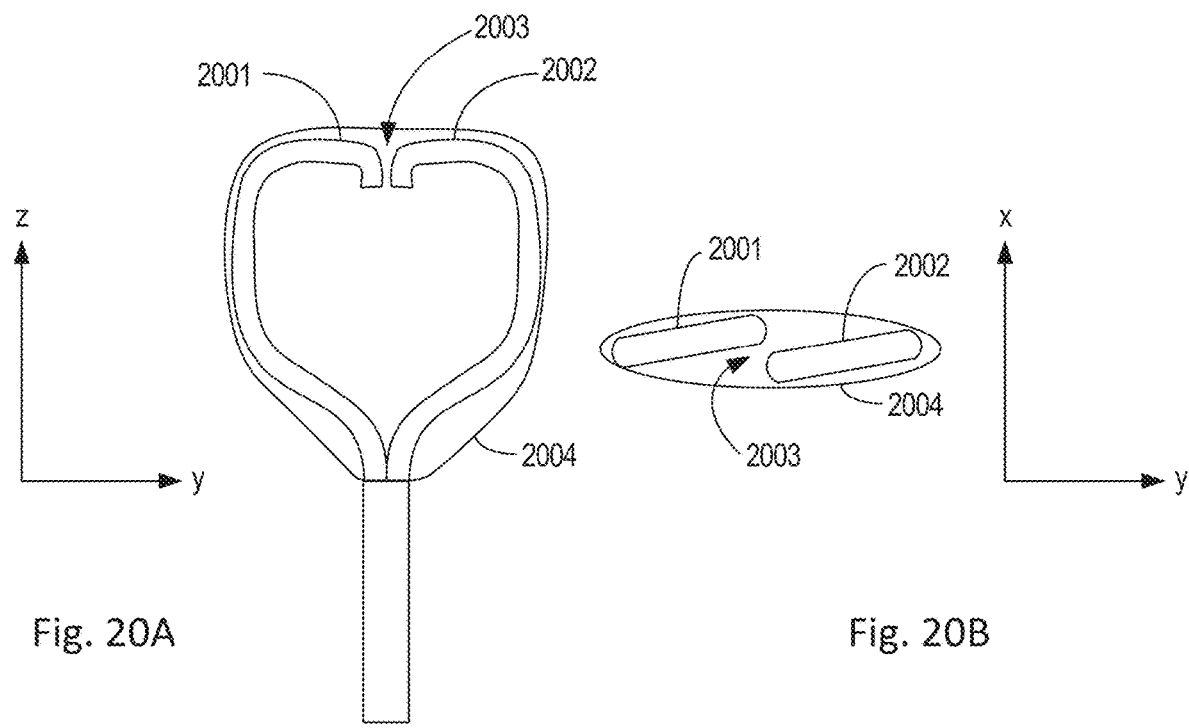
FIGS. 20A-20D illustrate an embodiment of an end effector member.
Figures 20C, 20D:
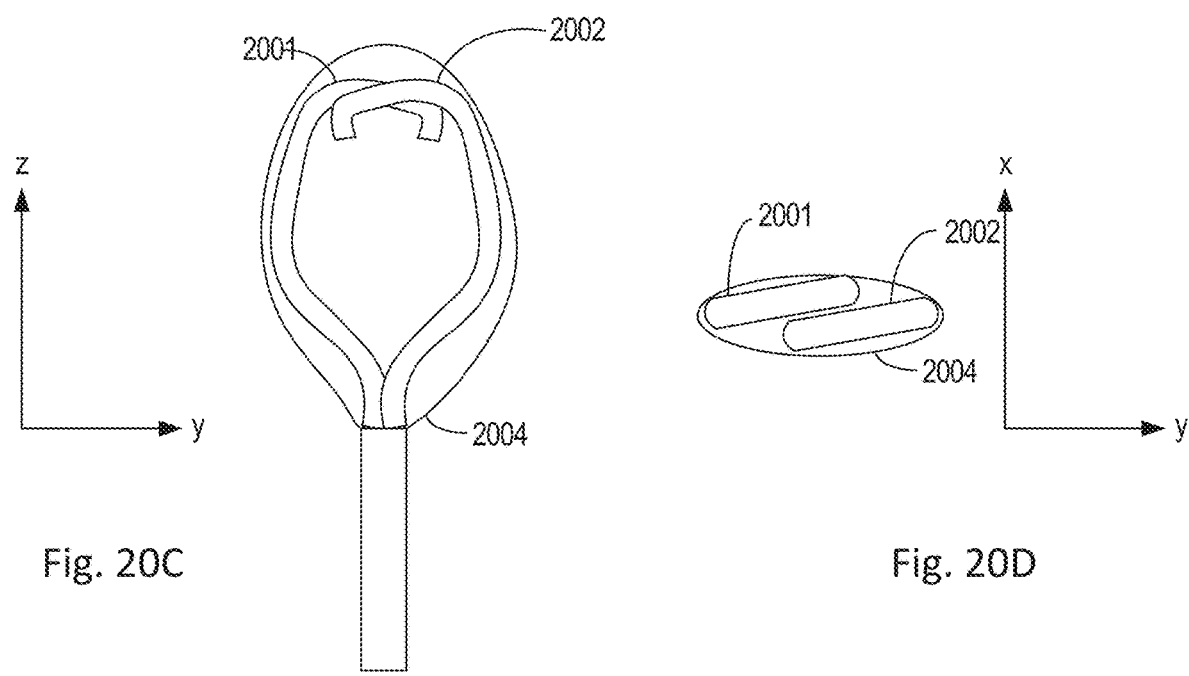

In embodiments, the end effector may include a flexible multi-part inner member that defines the outer shape of outer film of the end effector creating the surface area for treatment. FIGS. 20A-20D shows an end effector with a multi-part inner member. As shown, the inner member comprises a first member 2001 and a second member 2002 within an outer film 2004. In embodiments it is desirable to have an end effector with a large surface area, however the dimension of the end effector perpendicular to the longitudinal axis, along the Y axis in FIGS. 20A-20D, may be a limiting factor as it must comfortably fit into the nostril and through narrow portions of the nasal cavity prior to reaching the middle meatus. The flexibility of the inner member is configured to bend around rigid structures but is sufficiently stiff to maneuver through the nasal cavity and compress mucosa. In embodiments, first member 2001 and second member 2002 are substantially semi-circular in shape. First member 2001 and second member 2002 may extend longitudinally away from a distal end of a shaft and then include a curved portion initially curving away from a longitudinal axis of the shaft and then curving toward the longitudinal axis of the shaft. The distal ends of the first member 2001 and second member 2002 include bends which form an atraumatic tip to prevent damage to the patient and outer film. As shown, in the y-plane the first member 2001 and second member 2002 form a heart shape in the expanded configuration and may have a width of between 10 mm to 20 mm. In embodiments, first member 2001 and second member 2002 are configured to be able to bend toward each other and overlap each other when sufficient pressure as applied, as shown in FIGS. 20C and 20D. When overlapped, the dimension perpendicular to the longitudinal axis of the probe is reduced, for example the dimension may be reduced in a range of 1 mm to 8 mm. When overlapped in the compressed configuration, in the y plane that first member 2001 and second member 2002 form an oblong shaped profile. The force needed to overlap the first and second members 2001 and 2002 may be configured to be a force which is comfortable for the nostril to apply. When the compressed end effector enters the middle meatus the first and second member are biased back to an expanded orientation and the end effector has a larger area than could comfortably be introduced through the nostril with a rigid inner member. The compressing feature of the inner member is achieved by having the first member 2001 and second member 2002 shaped with a gap 2003 between them in the expanded configuration, shown in FIGS. 20A and 20B. Further, as shown, first member 2001 and second member 2002 are offset so they can compress inwards towards each other or beside each other. In embodiments, the gap 2003 will range from 1-5 mm. The inner member can be made of stainless steel or nitinol wire with a diameter <0.022" or high durometer polymer such as nylon 6, TR55, or the like. In embodiments, the inner member is made of stainless steel wire ranging from 0.010-0.020" in diameter. The stainless steel wire is ideal as it leaves the center of the end effector open to minimize the chance of ice crystals being formed and causing blockage of the cryogen line and stainless steel material properties are stable at temperatures below 0 deg. C.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating a tissue region within a nasal cavity of a patient, the method comprising:
    inserting a distal end of a surgical probe into the nasal cavity of the patient through a nostril of the patient in a first configuration, wherein the surgical probe comprises an outer shaft, an inner shaft positioned within a lumen of the outer shaft and translatable relative to the outer shaft, and an end effector coupled to a distal end of the inner shaft, wherein, in the first configuration, the inner shaft is in a proximal-most position relative to the outer shaft, wherein the end effector is coupled to the distal end of the inner shaft at a non-zero angle relative to a longitudinal axis of the distal end of the inner shaft in the first configuration, and wherein a distal portion of the inner shaft in the first configuration is substantially aligned with a longitudinal axis of the outer shaft and the end effector is positioned a first distance from a distal end of the outer shaft such that an entirety of the end effector is positioned distal to the lumen of the outer shaft in the first configuration;
    advancing the distal end of the surgical probe into the nasal cavity with the surgical probe in the first configuration;
    translating the inner shaft relative to the outer shaft so that the surgical probe is deployed to a second configuration, wherein the end effector is translated longitudinally to a second distance greater than the first distance away from the distal end of the outer shaft and laterally away from the longitudinal axis of the outer shaft, wherein the end effector in the second configuration is positioned within proximity of the tissue region having at least one posterior nasal nerve; and
    ablating the at least one posterior nasal nerve of the tissue region with the end effector.

2. The method of claim 1, further comprising initially contacting the end effector with an anatomical feature of a middle meatus to a lateral wall of the nasal cavity prior to translating the inner shaft relative to the outer shaft.

3. The method of claim 2, wherein translating the inner shaft relative to the outer shaft further comprises translating from a posterior portion of the tissue region to an anterior portion of the tissue region so that a surface of the end effector successively increases lateral contact with the tissue region.

4. The method of claim 3, wherein the first distance of the end effector from the distal end of the outer shaft is a range from less than 10 mm and the second distance of the end effector from the distal end of the outer shaft is in a range from 5 mm to 20 mm.

5. The method of claim 3, wherein a lateral translation of the end effector away from the longitudinal axis of the outer shaft is in a range from 10 degrees to 90 degrees.

6. The method of claim 1, wherein the outer shaft comprises an angled tip defining an angle between the distal portion of the inner shaft in the second configuration and the longitudinal axis of the outer shaft.

7. The method of claim 1, wherein the inner shaft comprises a flexible or self-expandable material.

8. The method of claim 1, wherein the inner shaft comprises a biased stylet, wherein translating the biased stylet relative to the outer shaft deploys the surgical probe from the first configuration where the biased stylet is constrained by the outer shaft in a substantially straightened configuration to the second configuration where the biased stylet is unconstrained by the outer shaft in a curved configuration to articulate the end effector laterally away from the longitudinal axis of the of the outer shaft.

9. The method of claim 1, further comprising maintaining the outer shaft substantially stationary relative to the nostril while translating the inner shaft relative to the outer shaft.

10. The method of claim 1, wherein nostril stretching by the outer shaft is inhibited while translating the inner shaft relative to the outer shaft.

11. The method of claim 1, further comprising maintaining the outer shaft at an orientation substantially parallel to a sagittal plane of the patient while translating the inner shaft relative to the outer shaft.

12. The method of claim 1, wherein the end effector comprises an expandable structure coupled to the distal end of the inner shaft and an inner member is disposed at the distal end of the inner shaft extending within the expandable structure which encloses the inner member such that the inner member is unattached to an interior of the expandable structure.

13. The method of claim 12, further comprising introducing a cryogenic fluid into the expandable structure such that the expandable structure inflates from a deflated configuration into an expanded configuration against the tissue region, wherein the cryogenic fluid evaporates within the expandable structure so as to cryogenically ablate the at least one posterior nasal nerve.

14. The method of claim 13, further comprising maintaining the inner member against the interior of the expandable structure and the tissue region until the at least one posterior nasal nerve is cryogenically ablated.

15. The method of claim 12, wherein the inner member comprises a first member and a second member, wherein the inner member is configurable from an expanded configuration wherein the first member and second member define a first width of the end effector between the first member and the second member, to a compressed configuration wherein the first member and the second member define a second width of the end effector that is smaller than the first width.

16. The method of claim 15, wherein the inner member is in the compressed configuration when the distal end of the surgical probe is inserted into the nostril and in the expanded configuration when the end effector is positioned within the tissue region having the at least one posterior nasal nerve.

17. The method of claim 15, wherein the first width is in a range from 10 mm to 20 mm.

18. The method of claim 17, wherein the first member and second member do not overlap in the expanded configuration.

19. The method of claim 15, wherein the second width is in a range from 5 mm to 19 mm.

20. The method of claim 19, wherein the first member and second member overlap in the compressed configuration.

21. The method of claim 15, wherein the first and second members comprise a heart shape in the expanded configuration and an oblong shape in the compressed configuration.

22. The method of claim 12, wherein the inner member comprises a planar member having an elongate loop shape.

23. A surgical probe for treating a tissue region within a nasal cavity of a patient, the surgical probe comprising:
an outer shaft having a distal end configured for insertion into a nostril of the nasal cavity of the patient, the outer shaft having a longitudinal axis and a lumen therethrough;
an inner shaft positioned within the lumen of the outer shaft and translatable relative to the outer shaft; and
an end effector coupled to a distal end of the inner shaft, wherein a distal portion of the inner shaft is substantially aligned with the longitudinal axis of the outer shaft and the end effector is positioned a first distance from the distal end of the outer shaft such that an entirety of the end effector is positioned distal to the lumen of the outer shaft when the surgical probe is in a first configuration during insertion and advancement of the surgical probe into the nasal cavity, wherein, in the first configuration, the inner shaft is in a proximalmost position relative to the outer shaft wherein the end effector is coupled to the distal end of the inner shaft at a non-zero angle relative to a longitudinal axis of the distal end of the inner shaft in the first configuration, and wherein a translation of the inner shaft relative to the outer shaft configures the end effector longitudinally to a second distance greater than the first distance away from the distal end of the outer shaft and laterally away from the longitudinal axis of the outer shaft when the surgical probe is in a second configuration, wherein the end effector in the second configuration is in lateral contact with the tissue region having at least one posterior nasal nerve and is configured to ablate the at least one posterior nasal nerve.

24. The surgical probe of claim 23, where the end effector is configured to initially contact an anatomical feature of a middle meatus to a lateral wall of the nasal cavity prior to the translation of the inner shaft relative to the outer shaft.

25. The surgical probe of claim 24, wherein the end effector is configured to successively increase lateral contact with the tissue region from a posterior portion of the tissue region to an anterior portion of the tissue region during the translation of the inner shaft relative to the outer shaft.

26. The surgical probe of claim 23, wherein the first distance of the end effector from the distal end of the outer shaft is a range from less than 10 mm and the second distance of the end effector from the distal end of the outer shaft is in a range from 5 mm to 20 mm.

27. The surgical probe of claim 23, wherein the end effector is configured to translate away from the longitudinal axis of the outer shaft in a range from 10 degrees to 90 degrees.

28. The surgical probe of claim 23, wherein the outer shaft comprises an angled tip defining an angle between the distal portion of the inner shaft in the second configuration and the longitudinal axis of the outer shaft.

29. The surgical probe of claim 23, wherein the inner shaft comprises a flexible or self-expandable material.

30. The surgical probe of claim 23, wherein the inner shaft comprises a biased stylet, wherein the biased stylet is configured to translate relative to the outer shaft and configured to deploy the surgical probe from the first configuration where the biased stylet is constrained by the outer shaft in a substantially straightened configuration to the second configuration where the biased stylet is unconstrained by the outer shaft in a curved configuration to articulate the end effector laterally away from the longitudinal axis of the of the outer shaft.

31. The surgical probe of claim 23, wherein the end effector comprises an expandable structure coupled to the distal end of the inner shaft and an inner member is disposed at the distal end of the inner shaft extending within the expandable structure which encloses the inner member such that the inner member is unattached to an interior of the expandable structure.

32. The surgical probe of claim 31, wherein the expandable structure is configured to receive a cryogenic fluid into the expandable structure such that the expandable structure is configured to inflate from a deflated configuration into an expanded configuration against the tissue region, and wherein the expandable structure is configured so that the cryogenic fluid evaporates within the expandable structure so as to cryogenically ablate the at least one posterior nasal nerve.

33. The surgical probe of claim 31, wherein the inner member comprises a first member and a second member, wherein the inner member is configurable from an expanded configuration wherein the first member and second member define a first width of the end effector between the first member and the second member, to a compressed configuration wherein the first member and the second member define a second width of the end effector that is smaller than the first width.

34. The surgical probe of claim 33, wherein the inner member is configured to be in the compressed configuration when the distal end of the surgical probe is inserted into the nostril and in the expanded configuration when the end effector is positioned within the tissue region having the at least one posterior nasal nerve.

35. The surgical probe of claim 33, wherein the first width is in a range from 10 mm to 20 mm.

36. The surgical probe of claim 35, wherein the first member and second member are configured to not overlap in the expanded configuration.

37. The surgical probe of claim 33, wherein the second width is in a range from 5 mm to 19 mm.

38. The surgical probe of claim 37, wherein the first member and second member are configured to overlap in the compressed configuration.

39. The surgical probe of claim 33, wherein the first and second members comprise a heart shape in the expanded configuration and an oblong shape in the compressed configuration.

40. The surgical probe of claim 31, wherein the inner member comprises a planar member having an elongate loop shape.

41. The surgical probe of claim 23, wherein the end effector comprises a cryotherapy balloon, wherein the surgical probe further comprises a cryogenic fluid source coupled to the inner shaft and a lumen disposed in the inner shaft and in fluid communication with the cryogenic fluid source and an interior of the cryotherapy balloon.

42. The surgical probe of claim 23, wherein the end effector is coupled to a flexible inner shaft.

43. The surgical probe of claim 23, wherein the inner shaft has a curvature or bend located a distance proximally from the end effector, wherein the curvature or bend is preformed.

* * * * *